US011577071B2

(12) United States Patent
Hinman et al.

(10) Patent No.: US 11,577,071 B2
(45) Date of Patent: Feb. 14, 2023

(54) MOVING ELECTRODES FOR THE APPLICATION OF ELECTRICAL THERAPY WITHIN A TISSUE

(71) Applicant: PULSE BIOSCIENCES, INC., Hayward, CA (US)

(72) Inventors: Cameron D. Hinman, Thurmond, NC (US); Kevin L. Moss, Tracy, CA (US); David J. Danitz, San Jose, CA (US)

(73) Assignee: Pulse Biosciences, Inc., Hayward, CA (US)

( * ) Notice: Subject to any disclaimer, the term of this patent is extended or adjusted under 35 U.S.C. 154(b) by 63 days.

(21) Appl. No.: 16/980,347

(22) PCT Filed: Mar. 11, 2019

(86) PCT No.: PCT/US2019/021649
§ 371 (c)(1),
(2) Date: Sep. 11, 2020

(87) PCT Pub. No.: WO2019/177987
PCT Pub. Date: Sep. 19, 2019

(65) Prior Publication Data
US 2021/0038881 A1 Feb. 11, 2021

Related U.S. Application Data

(60) Provisional application No. 62/642,552, filed on Mar. 13, 2018.

(51) Int. Cl.
*A61B 34/30* (2016.01)
*A61N 1/05* (2006.01)

(52) U.S. Cl.
CPC ............ *A61N 1/0502* (2013.01); *A61B 34/30* (2016.02)

(58) Field of Classification Search
CPC .............................. A61N 1/0502; A61B 34/30
See application file for complete search history.

(56) References Cited

U.S. PATENT DOCUMENTS 6,326,177 B1 12/2001 Schoenbach et al.
6,763,264 B2 7/2004 Hofmann
(Continued)

FOREIGN PATENT DOCUMENTS

WO WO2004/082498 A1 9/2004

OTHER PUBLICATIONS

Garon et al.; In Vitro and In Vivo Evaluation and a Case Report of Intense Nanosecond Pulsed Electric Field as a Local Therapy for Human Malignancies; International Journal of Cancer; 121(3); pp. 675-682; Aug. 2007.
(Continued)

*Primary Examiner* — Ankit D Tejani
*Assistant Examiner* — Joshua Brendon Solomon
(74) *Attorney, Agent, or Firm* — Shay Glenn LLP

(57) ABSTRACT

Electrodes that are configured to apply energy within the tissue while moving relative to the tissue. The apparatuses (devices, assemblies, systems) described herein may be configured with one or more electrodes that may move slightly in oscillatory movement and/or rotation relative to the tissue. The apparatuses described herein may be used to apply energy to a patient while minimizing or preventing the unintended modification of the tissue adjacent to the electrode, such as by arcing.

25 Claims, 17 Drawing Sheets

(56) References Cited

U.S. PATENT DOCUMENTS

| | | |
|---|---|---|
| 7,767,433 B2 | 8/2010 | Kuthi et al. |
| 8,000,813 B2 | 8/2011 | Schoenbach et al. |
| 8,512,334 B2 | 8/2013 | Nuccitelli et al. |
| 8,822,222 B2 | 9/2014 | Beebe et al. |
| 9,101,764 B2 | 8/2015 | Nuccitelli et al. |
| 9,724,155 B2 | 8/2017 | Nuccitelli et al. |
| 9,999,467 B2 | 6/2018 | Moss et al. |
| 10,252,050 B2 | 4/2019 | Kreis et al. |
| 10,779,882 B2 | 9/2020 | Long |
| 10,799,285 B2 | 10/2020 | Mulholland |
| 10,850,095 B2 | 12/2020 | Ebbers et al. |
| 2004/0162551 A1 | 8/2004 | Brown et al. |
| 2005/0222565 A1 | 10/2005 | Manstein |
| 2006/0062074 A1 | 3/2006 | Gundersen et al. |
| 2008/0231337 A1 | 9/2008 | Krishnaswamy et al. |
| 2010/0038971 A1 | 2/2010 | Sanders et al. |
| 2011/0009929 A1* | 1/2011 | Nuccitelli ............ A61N 1/0412 607/2 |
| 2011/0092973 A1 | 4/2011 | Nuccitelli et al. |
| 2014/0052126 A1 | 2/2014 | Long et al. |
| 2014/0364797 A1 | 12/2014 | Schoenbach et al. |
| 2015/0025604 A1 | 1/2015 | McClellian |
| 2015/0201991 A1 | 7/2015 | Zemlin |
| 2017/0080166 A1* | 3/2017 | Bagwell ............ A61B 17/3403 |
| 2017/0245928 A1 | 8/2017 | Xiao et al. |
| 2017/0246455 A1 | 8/2017 | Athos et al. |
| 2017/0319851 A1 | 11/2017 | Athos et al. |
| 2018/0050196 A1 | 2/2018 | Pawsey |
| 2018/0078755 A1 | 3/2018 | Kreis et al. |
| 2018/0243558 A1 | 8/2018 | Athos et al. |
| 2019/0059932 A1* | 2/2019 | Isosaki ............... A61B 18/1445 |
| 2019/0069957 A1* | 3/2019 | Barral .................... G06N 20/10 |
| 2019/0217080 A1 | 7/2019 | Moss et al. |
| 2019/0307500 A1* | 10/2019 | Byrd ...................... A61B 34/20 |
| 2020/0085491 A1* | 3/2020 | Goliszek .............. A61B 18/042 |

OTHER PUBLICATIONS

Wang et al.; Solid-State High Voltage Nanosecond Pulse Generator; IEEE InPulsed Power Conference;pp. 1199-1202; 4 pages; Jun. 13, 2005.

International Search Report and Written Opinion dated Jun. 14, 2019 for PCT/US2019/021649; 15 pages.

* cited by examiner

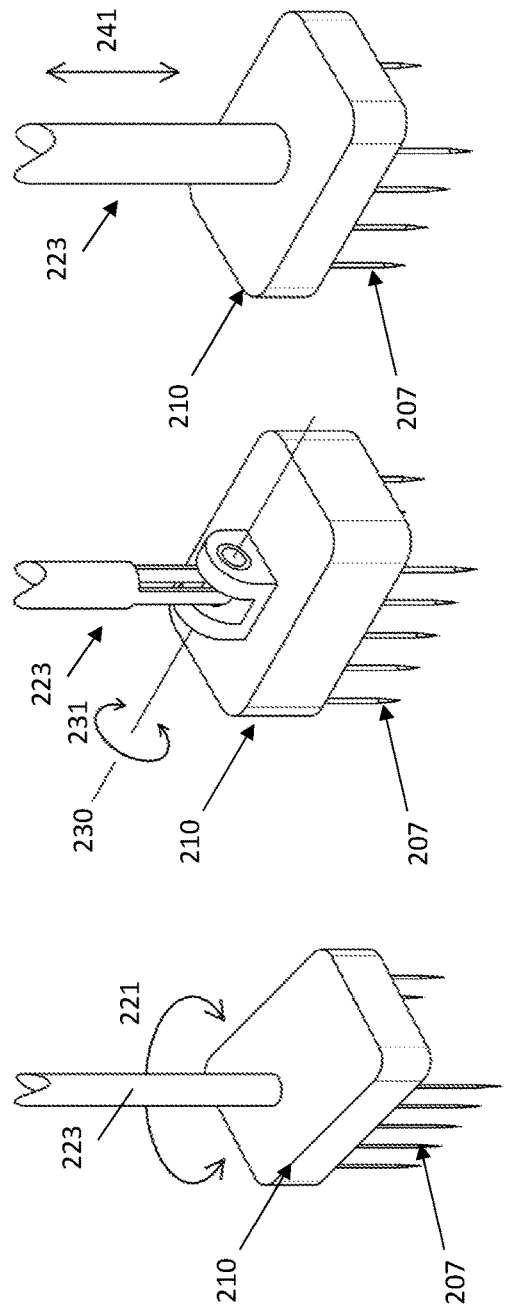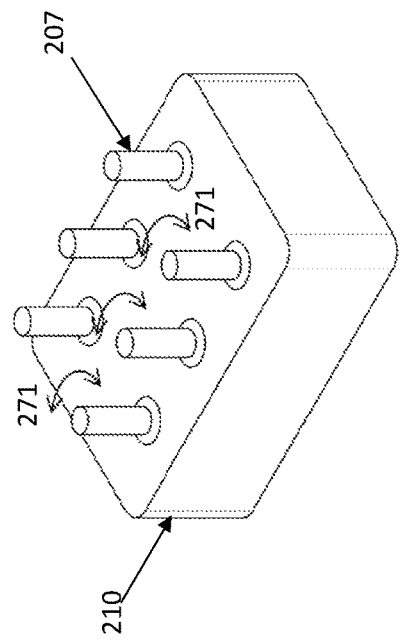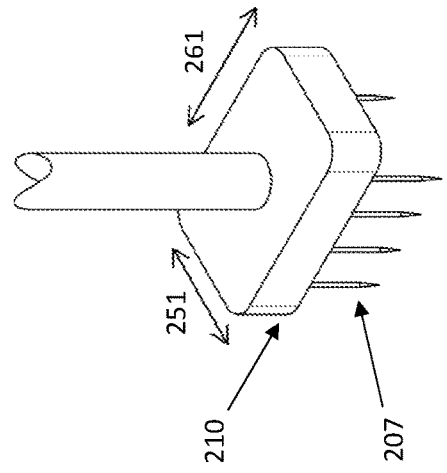

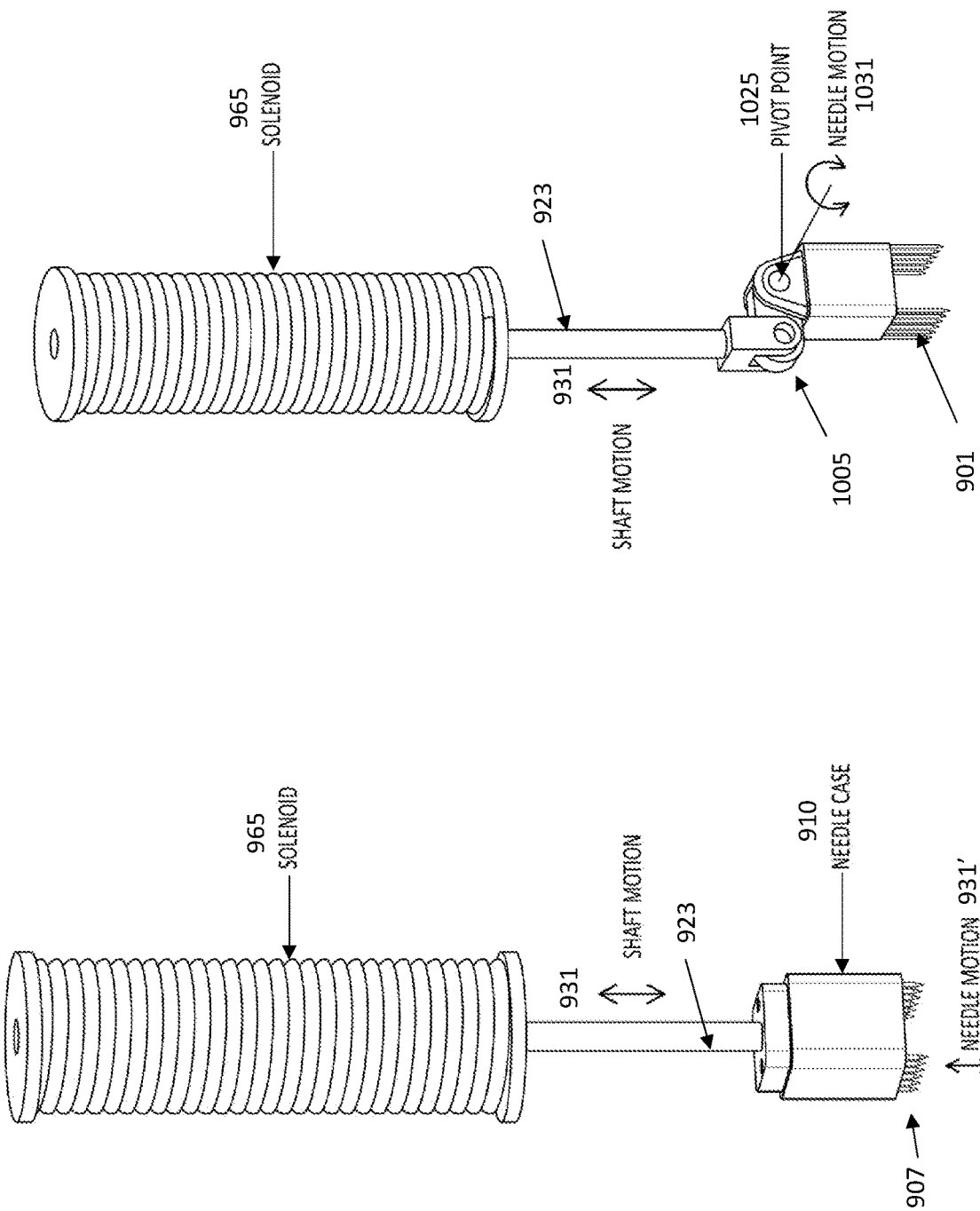

MOVING ELECTRODES FOR THE APPLICATION OF ELECTRICAL THERAPY WITHIN A TISSUE

CROSS REFERENCE TO RELATED APPLICATIONS

This patent application is a 371 of International Patent Application No. PCT/US2019/021649, filed Mar. 11, 2019, titled "MOVING ELECTRODES FOR THE APPLICATION OF ELECTRICAL THERAPY WITHIN A TISSUE," now International Publication No. WO 2019/177987, which claims priority to U.S. Provisional Patent Application No. 62/642,552, titled "MOVING ELECTRODES FOR THE APPLICATION OF ELECTRICAL THERAPY WITHIN A TISSUE," filed Mar. 13, 2018 and herein incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

The methods and apparatuses described herein may be related to electrodes for the application of electrical energy to a subject, for example, a patient. More specifically, the methods and apparatuses described herein relate to the electrodes that move within the tissue (e.g., vibrate, rotate, translate, and/or oscillate) during an electrical treatment of an internal tissue. These apparatuses and methods may be particularly useful for avoiding or minimizing undesirable electrical modification of the tissues by preventing electrical arcing.

BACKGROUND

Electrical energy may be applied within the tissue for a variety of purposes, including for the treatment of medical conditions. Electrical energy may be provided through an electrode that is inserted and/or implanted into the tissue. In some cases, the application of electrical energy by an electrode may result in the undesirable modification of the tissue at or around the electrode. Such tissue modifications may include changing the tissue impedance, such as by dehydration, which may make the application of electrical energy less controlled and predictable. For example, energy, and particularly high-voltage or high power energy, applied to the tissue may progressively change the impedance of the surrounding tissue in some regions near the electrode; at some point, the change in tissue impedance may result in an uncontrolled electrical discharge, such as an arc.

Although some systems are configured to monitor the tissue response so that the applied energy may be adjusted in order to avoid uncontrolled discharges, these solutions are not ideal, as they may simply limit the application and/or rate of application of energy to the tissue and may require discontinuing or suspending treatment. This may prolong treatment times, lower treatment dosing to less than needed or desired, or even cause premature discontinuation of the treatment.

This problem may be particularly acute when applying rapid, high-energy pulses, e.g., to treat patients. For example, nanosecond high voltage pulse generators have been described for biological and medical applications. See: Gundersen et al. "Nanosecond Pulse Generator Using a Fast Recovery Diode", IEEE 26th Power Modulator Conference, 2004, pages 603-606; Tang et al. "Solid-State High Voltage Nanosecond Pulse Generator," IEEE Pulsed Power Conference, 2005, pages 1199-1202; Tang et al. "Diode Opening Switch Based Nanosecond High Voltage Pulse Generators for Biological and Medical Applications", IEEE Transactions on Dielectrics and Electrical Insulation, Vol. 14, No. 4, 2007, pages 878-883; Yampolsky et al., "Repetitive Power Pulse Generator With Fast Rising Pulse" U.S. Pat. No. 6,831,377; Schoenbach et al. "Method and Apparatus for Intracellular Electro-Manipulation", U.S. Pat. No. 6,326,177; Gundersen et al., "Method for Intracellular Modifications Within Living Cells Using Pulsed Electric Fields", U.S. Patent Application No. 2006/0062074; Kuthi et al., "High Voltage Nanosecond Pulse Generator Using Fast Recovery Diodes for Cell Electro-Manipulation", U.S. Pat. No. 7,767,433; Krishnaswamy et al., "Compact Subnanosecond High Voltage Pulse Generation System for Cell Electro-Manipulation", U.S. Patent Application No. 2008/0231337; and Sanders et al. "Nanosecond Pulse Generator", U.S. Patent Application No. 2010/0038971. The entire content of these publications is incorporated herein by reference.

Because of the extremely high therapeutic voltages, as well as the very fast pulse times, applicators for delivery of such nanopulse stimulation devices must be configured so as to avoid or at least minimize arcing between the applicators. In some cases, the applicator may be configured to penetrate into the tissue and may include multiple needle-type electrodes. Such applicators may be particularly difficult to use with high-voltage systems while avoiding undesirable arcing. For example, when using a needle electrode, a small corona discharge can occur at locations of high current density on the needle (i.e., the very tip of the sharpened needle, or a sharpened needle edge on a trocar-shaped needle, or the transition between exposed needle/metal and insulation on the needle/metal). As the treatment progresses, the corona discharge during each pulse may start to break down the tissue.

Another issue referred to as "tenting" may occur when electrodes, and particularly needle electrodes, are inserted into the tissue; the tissue that is being penetrated by the electrode may stretch around the electrode(s) as pressure is applied. This may form an air gap (shaped like a tent) around the electrode. This issue may be exacerbated with multiple needle electrodes adjacent to each other, in which the tissue gap (tent) around one needle can overlap with the tissue gap (tent) of neighboring needle electrodes, forming a larger gap than with a single needle electrode. This tenting effect can also lead to arcing, particularly at the surface of the tissue.

The methods and apparatuses described herein may address various issues raised above.

SUMMARY OF THE DISCLOSURE

Described herein are apparatuses and methods for applying electrical energy to a subject's tissue using one or more electrodes configured to move within the tissue to prevent or limit unintended modification of the tissue adjacent to the electrode, such as by arcing. In general, described herein are implantable and/or insertable electrodes that may be moved (e.g., by rotation, oscillation, vibration, translation, etc.) during the application of energy to the tissue in order to reduce or eliminate arcing. Any of these apparatuses may also be configured to move (e.g., rotate, translate, oscillate, vibrate, etc.) the one or more electrodes before, during, or after the application of energy, to assist in inserting and/or removing the electrode(s) from the tissue while avoiding or minimizing tenting.

Any of these apparatuses may be configured as a device or a system, including, for example, a hand-held or hand-operated device, a computer-controlled, and/or a robotically operated, or remotely operated device. These apparatuses may be configured with one electrode or more than one electrode. The electrode may be, e.g., an array of electrodes. The electrodes described herein are generally insertable and/or implantable electrodes. For example, the electrodes may be one or more penetrating (e.g., needle, blade, etc.) electrodes. The electrodes may be configured for acute treatment (e.g., insertion into the tissue for the duration of a treatment or thereabouts) or for chronic treatment (e.g., implantation into the tissue). Any appropriate penetrating electrode may be used; in general a penetrating electrode may be any electrode that is configured or adapted for insertion into the tissue. Penetrating electrodes may be configured to penetrating into and/or through the tissue. Penetrating electrodes may be sharp and/or cutting, and may include a leading tissue-penetrating edge. Examples of penetrating electrodes include, but are not limited to needle electrodes. In general a penetrating electrode may be configured to deliver energy (electrical energy) from all or a portion of the electrode. The penetrating electrode may be electrically insulated over one or more regions. The non-insulated portions may be referred to uninsulated and may be configured as energy delivery regions of the electrode. Although in some variations the penetrating electrode may include a single energy delivery region, in some variations a penetrating electrode may include multiple energy delivery regions.

In any of the apparatuses described herein, the one or more electrodes are moved during the application of electrical energy. The movement may be one or more of the following: rotation (e.g., around a central axis of a set of electrodes or around each individual electrode, and may be in one direction or back-and-forth), translational oscillation (which may include vibration), and/or non-oscillating translation (and particularly small translation), movement. Rotation may be about any axis of the electrode (e.g., in pitch, roll, and/or yaw). Translational oscillation and non-oscillating translational movements may be made in any appropriate direction or combination of directions, such as: up/down, in/out, left side/right side, pitch, tilt, yaw, etc. The movements may be made in any combination of rotation and/or translational oscillation and/or non-oscillating translation. The amount of movement of the one or more electrodes being moved may be relatively small compared to the size of the tissue being treated and/or to the size of the penetrating electrode. For example, the translational oscillation may move the electrode(s) by less than about 4 mm, less than about 3 mm, less than about 2 mm, less than about 1 mm, less than about 0.8 mm, less than about 0.6 mm, less than about 0.5 mm, less than about 0.3 mm, less than about 0.1 mm, less than about 0.05 mm, less than about 0.001 mm, etc.).

The rate of rotation or rate of oscillation in the tissue may be about 0.01 Hz or greater, (e.g., about 0.05 Hz or greater, about 0.1 Hz or greater, about 0.5 Hz or greater, about 1 Hz, about 2 Hz or greater, about 3 Hz or greater, about 4 Hz or greater, about 5 Hz or greater, about 10 Hz or greater, about 20 Hz or greater, about 30 Hz or greater, about 40 Hz or greater, about 50 Hz or greater, about 100 Hz or greater, about 200 Hz or greater, etc., e.g., between about 0.01 Hz and about 10 kHz, between about 0.1 Hz and about 1 kHz, etc.).

For example, described herein are devices for the delivery of electrical therapy (electrical therapy devices) that may include: one or more penetrating electrodes; and a driver coupled to the one or more penetrating electrodes, wherein the driver is configured to rotate, translationally oscillate, and/or non-oscillatory translate the one or more penetrating electrodes; and a power connector configured to electrically connect the one or more needle electrodes to a power source.

Also described herein are treatment tips (e.g., treatment tip devices) that may include one or more electrodes (e.g., needle electrodes) that may be held by a frame (e.g., electrode frame) configured to allow the electrodes to move when driven by a driver. In some embodiments, the same or a different housing (e.g. tip housing) or frame may be moved relative to the one or more electrodes. The electrodes may be coupled to a linkage directly or through the frame (or an electrode block that is configured to move with the electrodes). The linkage may be connected to the driver, or to a portion of the driver, or the treatment tip may include a driver coupler for coupling to the driver. The treatment tip may also include an electrical connector for connecting to a source of electrical energy. For example, the power connector may be configured to electrically connect the one or more needle electrodes to a power source configured to apply high voltage power to the one or more needle electrodes having a peak voltage of between about 100 volts per centimeter (e.g., 0.1 kV/cm) and about 500 kV/cm (e.g., between about 0.5 kV/cm and about 500 kV/cm, between about 1 kV/cm and about 500 kV/cm, greater than about 0.1 kV/cm, greater than about 0.5 kV/cm, greater than about 1 kV/cm, etc.).

In general, a treatment tip may include any number of electrodes, including needle electrodes. For example, the treatment tip may include a plurality of needle electrodes.

Any appropriate driver may be used to drive movement of the electrodes. For example, the driver may be configured to move (e.g., rotate and/or oscillate and/or non-oscillatory translate) the one or more needle electrodes while applying energy through the one or more needle electrodes to a tissue.

As mentioned, any of these apparatuses may include a linkage coupling the driver to the one or more needle electrodes. The linkage may be configured to translate the movement of the driver into rotation and/or translational oscillation of the one or more needle electrodes. Examples of linkages may include (but are not limited to): a flexible shaft, one or more gears, a lead screw, and/or a lead nut, etc. For example, a linkage may be configured to translate movement of the driver into rotation of the one or more needle electrodes about a central axis of each of the one or more needle electrodes. For example, a linkage may be configured to translate the movement of the driver into oscillatory movement in the long axis of each of the one or more needle electrodes. A linkage may be configured to translate the movement of the driver into oscillatory side-to-side movement of each of the one or more needle electrodes. A linkage may be configured to translate the movement of the driver into oscillatory pitch, yaw or tilt movement of each or some of the one or more needle electrodes.

Any appropriate driver may be used. For example, a driver may be a motor configured to move (e.g., rotate and/or oscillate and/or non-oscillatory translate) the electrode(s). A driver may be a solenoid configured to drive oscillation of the one or more needle electrodes. A driver may be a piezoelectric material, a driver may be one or more electromagnetic coils configured to move a magnet. The drive may be a shape-memory alloy (SMA) actuator.

In general, the driver may be configured to rotate and/or translationally oscillate the one or more needle electrodes at greater than about 0.01 Hz. For example, the driver may be configured to rotate and/or translationally oscillate the one or more needle electrodes at between 0.01 Hz and 10 kHz (e.g., between about 0.01 Hz and 1 kHz, between about 0.1 Hz and 10 kHz, between about 0.1 Hz and 1 kHz, greater than about 0.1 Hz, etc.)

In some embodiments, a treatment tip device for delivery of electrical therapy may include: one or more needle electrodes; a linkage connected to the one or more needle electrodes; and a driver coupled to the one or more needle electrodes through the linkage, wherein the driver is configured to move and the linkage is configured to translate the movement of the driver into rotation and/or translational oscillation of the one or more needle electrodes at greater than 0.01 Hz. The treatment tip device may also include a power connector configured to electrically connect the one or more needle electrodes to a power source, wherein the device is further configured to rotate and/or translationally oscillate the one or more needle electrodes as energy is delivered through the needle electrodes.

According to another aspect, also described herein are methods of applying electrical therapy to a subject. For example, any of these methods may include: inserting one or more electrodes into the subject's tissue; and applying energy to the subject's tissue from the one or more electrodes while preventing arcing by moving (e.g., rotating and/or translationally oscillating and/or translating without oscillating) the one or more electrodes within the subject's tissue. The movement may be relative to the tissue. Any of the methods described herein may also or alternatively be methods to treat a tissue by moving (e.g., rotating and/or translationally oscillating and/or translating without oscillating) the one or more electrodes to prevent arcing.

In some embodiments the methods may include moving (e.g., rotating and/or translationally oscillating and/or translating without oscillating) one or more electrodes as they are inserted to avoid or at least reduce tenting of the tissue.

Moving the one or more needle electrodes may include rotating and/or translationally oscillating and/or translating without oscillating the one or more needle electrodes at greater than some minimum rate. When moving the tissue in rotation and/or translational oscillation, the rate may refer to the frequency of movement, and may be, for example, about 0.01 Hz or more. For example, rotating and/or translationally oscillating the one or more needle electrodes may include rotating and/or translationally oscillating the one or more needle electrodes at between about 0.01 Hz and about 10 kHz (e.g., between about 0.1 Hz and about 10 kHz, between about 0.1 Hz and 1 kHz, etc.). Rotating and/or oscillating the one or more needle electrodes may include rotating and/or mechanically oscillating the one or more needle electrodes at between 0.01 Hz and 1 kHz. Rotating and/or oscillating the one or more needle electrodes may include rotating the one or more needle electrodes about a central axis through each of the one or more needle electrodes. Alternatively or additionally, rotating and/or translationally oscillating the one or more needle electrodes may comprise moving the one or more needle electrodes in the long axis of each of the one or more needle electrodes. For example, rotating and/or translationally oscillating the one or more needle electrodes may comprise moving the one or more needle electrodes in an oscillatory side-to-side movement; also rotating and/or translationally oscillating the one or more needle electrodes may include moving the one or more needle electrodes in an oscillatory pitch, yaw or tilt movement.

The rate of motion of the one or more electrodes may be continuous, varying and/or pulsatile. For example, in some variations, the electrode(s) is/are moved continuously during the operation of the apparatus, e.g., during the application of energy by the apparatus. In some variations the apparatus is configured so that the electrode(s) are moved at a frequency that is not constant; for example, the electrode(s) may be moved, stopped, moved, stopped, etc. at a movement frequency (e.g., between 0.01 Hz and 10 kHz, about 0.1 Hz and 10 kHz, about 0.01 Hz and 1 kHz, about 0.1 Hz and 1 kHz, etc.). The movement frequency may be matched to the stimulation frequency at which energy is applied by the electrode(s) when the electrodes apply a pulsed energy therapy. For example, in some variations, the energy therapy is pulsed at a frequency and the electrodes are moved at the same frequency or a harmonic of this frequency; for example, the electrode(s) may be rotated and/or translationally oscillated and/or non-oscillatory translated only between some or all of the pulses of electrical energy being applied. Alternatively in some variations, the electrode(s) may be moved during the application of the energy therapy only during one or more of the pulses of energy (e.g., during the 'on' portion of the one or more pulses). In further variations, the electrode(s) may be moved every particular time interval, for example, every 10 seconds (either during application of energy or between pulses).

In general, the energy therapy may refer to the applied electrical energy. As used herein energy is applied by the electrode(s) during the application of energy therapy. The energy therapy may be continuous or pulsed. The energy therapy may be pulsed at a single frequency or a range of frequencies, including at a modulated frequency (e.g., having a carrier frequency).

As mentioned, any appropriate electrical energy may be applied while moving the electrodes relative to the tissue. For example, applying energy may comprise applying high-voltage nanosecond electrical pulses, such as applying a train of sub-microsecond electrical pulses having a pulse width of between 0.1 nanoseconds (ns) and 1000 nanoseconds (ns). Applying high-voltage nanosecond electrical pulses may comprise applying a train of sub-microsecond electrical pulses having peak voltages of between 10 kilovolts per centimeter (kV/cm) and 500 kV/cm. Applying high-voltage nanosecond electrical pulses may comprise applying a train of sub-microsecond electrical pulses at a frequency of between 0.01 (Hz) to 10,000 Hz. Applying energy may comprise applying microsecond electrical pulses, or picosecond electrical pulses.

The methods and apparatuses described herein may be used as part of any appropriate electrical therapy in which electrical energy is applied within the tissue (or in some cases on the tissue). For example, the method of applying energy described herein may be used to treat one or more of the following: organ tissue cancer (e.g., lung cancer, kidney cancer, pancreatic cancer, colon cancer, breast cancer, etc.), skin cancer, cherry angioma, warts, keloids/scars, aging skin, dermatological conditions and/or disease, molluscum angioma, necrobiosis lipoidica (NBL), melisma, lipoma epidermal/sebaceous cyst, basal cell carcinoma, any type of tumors or abnormal tissue growth (e.g., benign tumors, precancerous tumors). Alternatively, or additionally, these methods may be methods of any other body tissue, including non-skin tissue (respiratory tissue, lung tissue, breast tissue, liver tissue, etc.).

According to some embodiments, a method of applying electrical therapy to a subject may include: inserting one or more needle electrodes into the subject's tissue; and moving the one or more needle electrodes while applying energy to the subject's tissue from the one or more needle electrodes to move a point of high current density to a different location in the tissue to prevent arcing.

According to further embodiments, a method of applying electrical therapy to a subject may include: inserting one or more penetrating electrodes, such as needle electrodes, into the subject's tissue; and applying high-voltage electrically pulses having peak voltages of between 10 kilovolts per centimeter (kV/cm) and 500 kV/cm to the subject's tissue from the one or more needle electrodes while rotating and/or translationally oscillating and/or non-oscillatory translating the one or more needle electrodes within the subject's tissue at 0.01 Hz or greater (e.g., 0.05 Hz or greater, 0.1 Hz or greater, etc.).

For example, described herein are systems for delivery of electrical therapy, the system comprising: one or more penetrating electrodes configured to deliver electrical energy to a tissue; and a power connector configured to electrically connect the one or more penetrating electrodes to a power source; a driver coupled to and configured to move the one or more penetrating electrodes; and a controller configured to direct operation of the driver and to move the one or more penetrating electrodes when power is applied to the one or more penetrating electrodes or between pulses of pulsed applied power to the one or more penetrating electrodes.

The one or more penetrating electrodes may be, for example, one or more needle electrode and/or one or more blade electrodes.

Any of these systems may include a linkage coupling the driver to the one or more penetrating electrodes, wherein the linkage is configured to translate the movement of the driver into movement (e.g., rotation and/or translational oscillation, and/or non-oscillatory translation) of the one or more penetrating electrodes. For example, the linkage may be one or more of: a flexible shaft, one or more gears, a lead screw and/or nut, etc. The linkage may be configured to translate movement of the driver into rotation of the one or more penetrating electrodes about a central axis through each or at least some of the one or more penetrating electrodes. The linkage may be configured to translate the movement of the driver into oscillatory movement in the long axis of each or at least some of the one or more penetrating electrodes. The linkage may be configured to translate the movement of the driver into oscillatory side-to-side movement of each or at least some of the one or more penetrating electrodes. The linkage may be configured to translate the movement of the driver into oscillatory pitch, yaw or tilt movement of each or at least some of the one or more penetrating electrodes.

The driver may be configured to translationally oscillate the one or more penetrating electrodes. For example, the drive may be configured to rotate the one or more penetrating electrodes (e.g., in one direction or in oscillation, back and forth). The driver may comprise a motor configured to rotate and/or oscillate. Thus, the system may include a linkage between the one or more penetrating electrodes and the driver, wherein the linkage is configured to translate the rotation and/or oscillation of the motor into rotation and/or translational oscillation of the one or more penetrating electrodes. The driver may include a solenoid configured to drive movement (e.g., oscillation, non-oscillatory translation and/or rotation) of the one or more penetrating electrodes. For example, the system may include a linkage between the driver and the one or more penetrating electrodes, wherein the linkage is configured to translate movement of the solenoid into rotation and/or translational oscillation and/or non-oscillatory translation of the one or more penetrating electrodes. The driver may be one or more electromagnetic coils configured to move a magnet. The system may include a linkage between the one or more penetrating electrodes and the driver, wherein the linkage is configured to translate the movement of the magnet into rotation and/or translational oscillation and/or non-oscillatory translation of the one or more penetrating electrodes. The driver may be configured to rotate and/or translationally oscillate the one or more penetrating electrodes at greater than 0.01 Hz.

Any of the apparatuses described herein may include one or more housings enclosing and/or providing support for the components of the system, including the one or more electrodes, linkage, connectors, and/or driver. For example, any of the device or systems described herein may include a housing enclosing the driver and at least part of the one or more penetrating electrodes.

Any power connector may be configured to electrically connect the one or more penetrating electrodes to a power source configured to apply high voltage power to the one or more penetrating electrodes, such as (but not limited to) power having a peak voltage of between 10 kilovolts per centimeter (kV/cm) and 500 kV/cm.

Any of the apparatuses described herein may be configured as robotic apparatus (e.g., robotic device and/or robotic system). A robotic apparatus may incorporate any of the elements and features described herein. For example, the robotic apparatus may be part of a device for delivery of an electrical therapy that includes robotic actuator (e.g., robotic arm, etc.) and a processor/controller directing operation of the apparatus to deliver energy and to move to avoid or minimize arcing. The apparatus may also include one or more electrodes (e.g., needle electrodes) configured to deliver electrical energy to a tissue; and a driver coupled to the one or more needle electrodes, wherein the driver is configured to rotate and/or translationally oscillate and/or non-oscillatory translate the one or more needle electrodes. The driver may be formed entirely or in part by the robotic actuator.

For example, a robotic device for delivery of electrical therapy may include: a robotic actuator, a controller (e.g., processor), one or more needle electrodes, and in some variations, a linkage connected to the one or more needle electrodes. As mentioned, in some variations, the movement of the needles during the application of an energy therapy may be achieved through the robotic actuator, however in some variations, the apparatus may additionally include a driver coupled to the one or more needle electrodes through the linkage, wherein the driver is configured to move and the linkage is configured to translate the movement of the driver into rotation and/or translational oscillation and/or non-oscillatory translation of the one or more electrodes (e.g., at greater than 0.01 Hz). Any of these apparatuses may also include a power connector configured to electrically connect the one or more needle electrodes to a power source. In general, these apparatuses may be configured to rotate and/or translationally oscillate and/or non-oscillatory translate the one or more needle electrodes as energy is delivered through the needle electrodes or between pulses delivered by the needle electrodes.

Also described herein are treatment tip devices for delivery of electrical therapy. These devices may include: one or more needle electrodes configured to deliver electrical energy to a tissue; and a linkage coupled to the one or more needle electrodes, wherein the linkage is configured to rotate and/or translationally oscillate and/or non-oscillatory translate the one or more needle electrodes when driven by a driver; and a power connector configured to electrically connect the one or more needle electrodes to a power source. The device may also include a tip housing enclosing the linkage from which the one or more needle electrodes project, and/or a connector configured to couple the treatment tip to an applicator so that the power connector couples to a power source and the linkage couples to a driver when the treatment tip is engage with the applicator.

As mentioned above, the apparatuses described herein may include an appropriate driver or drivers. For example, the driver may be configured to drive a linkage to move the electrode(s), and/or the driver may be configured to drive all or some of the electrodes (when multiple electrodes are used) directly. Examples of drivers include, but should not be limited to: a motor, a piezoelectric driver, a magnetic driver, a shape memory actuator, etc.

Any of these apparatuses, including the treatment tips, may include a frame configured to hold the one or more needle electrodes in the treatment tip so that the linkage may move the one or more needle electrodes relative to the treatment tip. The frame may hold the electrode(s) but allow them to move. For example, the frame may be configured to allow rotational movement of the one or more electrodes and may prevent the electrode(s) from contacting or otherwise interfering with each other (e.g., holding them within the housing of the tip while allowing relative movement).

Any of the treatment tips described herein may not include a driver, but may instead provide connection to a linkage within the treatment tip that allows movement of the one or more electrodes. The connector may be a mechanical connector to couple the linkage to the driver. In some variations the treatment tip may include all or a portion of the driver. For example, the treatment tip may include a magnetic and/or paramagnetic component (magnetic driver) that is driven by a magnetic field within the reusable holder portion, to which the treatment tip attaches.

In general, any of the treatment tips described herein may be configured to be attached to a durable (e.g., reusable) base portion. This base portion may be referred to as a holder. The base (or holder) may be configured to be hand-held. As mentioned above, in some variations the holder may be part of a robotic system (e.g., robotic arm) or configured for attachment to the robotic arm. The base/holder may also include a housing (base housing or holder housing). The treatment tip may couple to the holder to attach it structurally to the holder, as well as electrically (to drive the application of electrical energy from the electrode(s), and in some variations mechanically (to couple to a linkage and/or driver). These various connectors may be compound connectors (e.g., transmitting both electrical and/or mechanical connectivity), or separate connectors.

Any of the apparatuses described herein may include a controller having one or more processors for controlling operation of the apparatus. The controller may control operation of the driver and/or the application of the electrical energy, and may coordinate both. The controller may be configured with software, firmware and/or hardware that allows it to control the operation of the apparatus. In particular, the controller of an electrical therapy device may include a non-transitory computer-readable storage medium storing a set of instructions capable of being executed by a processor of an electrical therapy apparatus, that, when executed by the processor, causes the electrical therapy apparatus to: apply, from one or more needle electrodes of the electrical therapy apparatus (for example, upon receipt of an operational instruction from an operator of the electrical therapy device) an energy therapy comprising one or more of pulsed electrical energy or continuous electrical energy; move, concurrently with the application, or between some of the pulses, of the energy therapy, the one or more needle electrode so that the one or more needle electrodes rotate and/or translationally oscillate and/or non-oscillatory translate.

The set of instructions, when executed by the processor, may further cause the processor to receive the operation instruction from the operator of the electrical therapy device. For example, the operation instructions may be 'on' control input, such as from a switch, button, foot petal, dial, etc. that may be on the device to activate operation of the device (e.g., application of energy concurrent with movement of the electrode(s). The set of instructions, when executed by the processor, may further causes the electrical therapy apparatus stop applying the energy therapy and to stop moving the one or more needle electrodes. For example, when the control input is released and/or switched to 'off'.

The set of instructions, when executed by the processor, may cause the electrical therapy apparatus to apply the energy therapy wherein the energy therapy comprises pulsed electrical energy or continuous electrical energy. For example, the pulsed electrical energy may comprise high-voltage nanosecond electrical pulses, as discussed above. The set of instructions, when executed by the processor, may cause the electrical therapy apparatus to rotate and/or translationally oscillate and/or non-oscillatory translate the one or more needle electrodes between pulses applied by the one or more needle electrodes.

Other features and advantages of the devices and methods of the present disclosure will become apparent from the following detailed description of one or more implementations when read in view of the accompanying figures.

BRIEF DESCRIPTION OF THE DRAWINGS

It should be noted that the drawings are not to scale and are intended only as an aid in conjunction with the explanations in the following detailed description. The sizes and relative positions of elements in the drawings are not necessarily drawn to scale. For example, the shapes of various elements and angles are not drawn to scale, and some of these elements are arbitrarily enlarged and positioned to improve drawing legibility. The novel features of the inventions described herein are set forth with particularity in the claims that follow. A better understanding of the features and advantages of the present methods and apparatuses will be obtained by reference to the following detailed description that sets forth illustrative embodiments, and the accompanying drawings of which:

FIGS. 2A-2F illustrate examples of movement of the electrodes that may be used in any of the apparatuses described herein.

FIG. 4 shows a side view and

FIG. 5 a bottom view.

FIGS. 9 and 10 illustrate assemblies for oscillating a plurality of needle electrodes that are each driven by a solenoid.

DETAILED DESCRIPTION

Figure 1B:
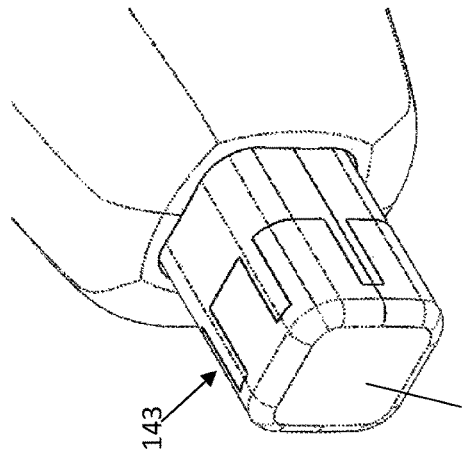
FIGS. 1B and 1C illustrate one example of a distal tip of an apparatus such as the one shown in FIG. 1A, in which the electrodes are configured as needle electrodes that may be protected by a retractable tip (electrode housing) that may also insulate the electrodes.

For the sake of clarity and conciseness, certain aspects of components or steps of certain embodiments are presented without undue detail where such detail would be apparent to skilled persons in light of the teachings herein and/or where such detail would obfuscate an understanding of more pertinent aspects of the embodiments.

According to one aspect of the disclosure, described herein are electrodes that are configured to apply energy within the tissue while moving to prevent or minimize/reduce arcing. Without being bound by any particular theory of operation, it is hypothesized that the apparatuses (devices and systems) described herein may reduce electrical inhomogeneities that may lead to arcing. These apparatuses may move the electrode relative to the tissue so that the tissue in peak electric field areas (where corona forms) changes during the application of electrical energy. The movement may be in a rotational and/or cyclical (oscillatory) manner, or in a non-oscillatory translation manner. As discussed above, a small corona discharge can occur at locations of high current density on an electrode in the tissue. When the electrode is held in a relatively fixed positon relative to the tissue, the corona is occurring at the same point(s) along the electrode which may locally modify (e.g., break down) that tissue. Thus, when pulsing, particularly a high voltage, each pulse may be changing the local electrical properties of the tissue. The electrodes described herein are configured to move in such a manner within the tissue when applying energy (including pulsed energy) which may move the point(s) of corona formation to different regions of the tissue, preventing or delaying local modification of the tissue that may lead to rapid changes in the electrical properties, including arcing. By moving (e.g., rotating and/or oscillating and/or non-oscillatory translating) the one or more electrodes (including, but not limited to, needle electrodes), the application of energy within the tissue may be made more uniform and predictable.

It is possible that moving the electrode(s) as described herein may prevent a change or break down on the tissue due to local effects of the electrical energy on the tissue adjacent to the electrode(s).

The electrodes may be moved in any direction, including one or more of: in and out, side to side, etc. For example, when applying pulses of electrical energy (e.g., in some cases high-voltage energy) to the tissue with an electrode, moving the electrode location slightly within the tissue (e.g., between each pulse of electrical energy), the corona point(s) may be moved to fresh tissue regions for each pulse so that the tissue never gets a chance to break down over the course of the treatment.

Thus, moving the electrodes (e.g., needle electrodes) of an electrical applicator tip of a device for delivering electrical therapy as described herein may reduce the likelihood of arcing and other tissue inhomogeneities when applying electrical energy. Further, the apparatuses described herein may also prevent or reduce problems (including potential arcing) due to insertion of the electrodes through the tissue and may also prevent the formation of air pockets due to tenting when inserting or operating the electrode(s) in tissue. For example, by moving the one or more electrodes prior to the application of energy to reduce buckling or pinching of tissue, particularly near adjacent electrodes when applied into the tissue. This may reduce the likelihood that an arc will occur.

In general, the electrodes described herein may be part of a treatment tip device for delivery of electrical therapy. The treatment tip device may also be referred to as simply a "treatment device for delivery of electrical energy". Typically, the one or more movable (e.g., oscillating, vibrating, rotating, etc.) electrodes may be present at the tip, which may be referred to as the distal end, of the device.

Although the device and apparatuses described herein are primarily illustrated and described for use in implantable or inserted electrodes, such as needle electrodes, these methods and apparatuses may also be used with one or more external, e.g., surface, electrodes. For example, the methods and apparatuses described herein may be used with one or more skin-surface electrodes configured to prevent arcing by moving (e.g., oscillating and/or rotating, and/or non-oscillatory translation) while applying an energy therapy.

A typical apparatus may include one or more electrodes. In particular, the electrodes may be tissue penetrating, such as (but not limited to) needle electrodes. When multiple electrodes are included, they may be arranged as an array (e.g., a line, grid, parallel lines, etc.). The apparatus also typically includes a driver that is coupled to the one or more electrodes and is configured to rotate and/or translationally oscillate the one or more electrodes. The driver may be directly or indirectly coupled to the one or more electrodes (e.g., through a linkage and/or stage). When a plurality of electrodes is used, the electrodes may be jointly and/or individually moved. Any of these apparatuses may also include one or more power connectors that are configured to electrically connect the one or more needle electrodes to a power source. For example, the power connectors may be configured to connect to a source of pulsed electrical power, including (but not limited to) a source for nanosecond (ns) high voltage pulses (e.g., a nanosecond high voltage pulse generators, as mentioned above).

For example, a treatment tip device for delivery of electrical therapy may include one or more electrodes (e.g., needle electrodes), and a linkage connected to the one or more needle electrodes that couples the needle electrodes to a driver through the linkage, wherein the driver is configured to move and the linkage is configured to translate the movement of the driver into rotation and/or translational oscillation of the one or more needle electrodes (e.g., at greater than 0.01 Hz). The device may also include a power connector configured to electrically connect the one or more needle electrodes to a power source. In general, any of these devices is also configured to rotate and/or translationally oscillate the one or more needle electrodes as energy is delivered through the needle electrodes. For example, the controls for controlling the application of electrical energy through the electrodes may be configured to concurrently engage the driver and when energy is applied by the apparatus, or at least between concurrent pulses of energy (when pulsed energy is used).

Figure 1C:
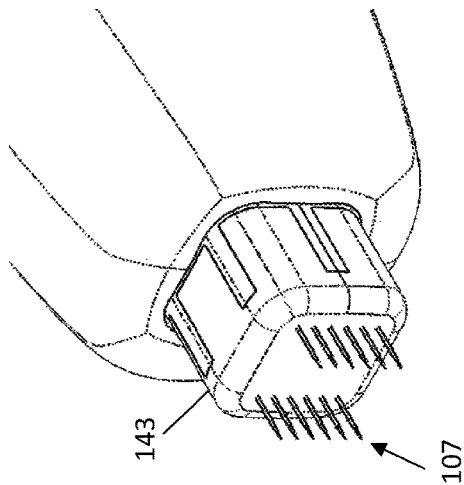
Figure 1A:
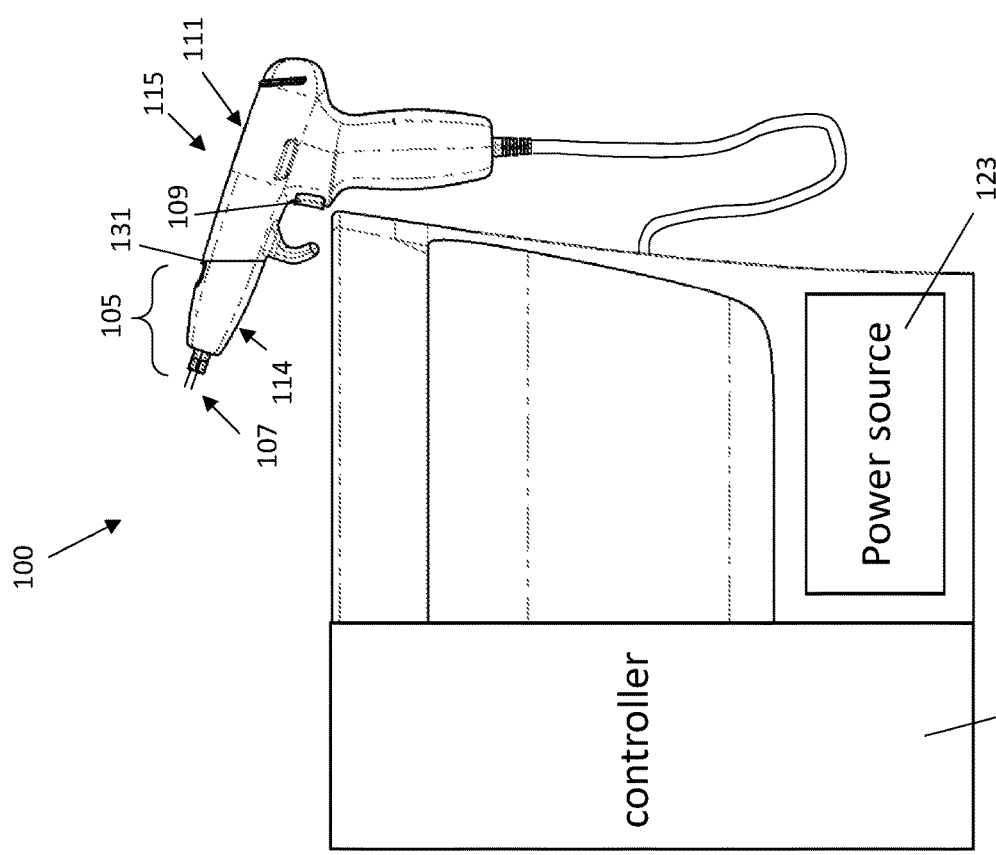
FIG. 1A is an example of an apparatus configured as a system for applying energy using needle electrodes that are configured to move relative to the tissue while applying the energy.

FIG. 1A illustrates one example of a treatment tip device 105 for delivery of electrical therapy. In this example, the treatment tip device 105 is shown as part of a system 100 for delivery of electrical therapy. The treatment tip in this example includes a plurality of electrodes 107 that extend distally from the distal end of the treatment tip. The treatment tip may be removable (and in some configurations, single-use or low-use), and may be disposable or reusable, e.g., after cleaning and/or sterilizing. In this example, the treatment tip may be removably coupled to a holder portion or holder 115 that is configured to be hand-held. This holder includes a control (button/switch) 109 that sends a command signal to the controller (e.g., processor) 121 to start and/or stop the apparatus. Multiple controls may be included. The needle electrodes may be coupled directly or indirectly to a driver, e.g. a motor (not shown), which is not visible through the housing 111 of the holder (e.g., base) in FIG. 1A. The holder housing 111 may be connected to or configured for being held in a user's hand, as shown, or it may be adapted for connection to another delivery tool, including a robotic arm, as shown by example in FIG. 17.

In variations in which the treatment tip is removable, the needle electrodes may be held in place by a frame coupled to the treatment tip housing 114 that allows the one or more needle electrodes to move relative to the tissue, and/or the tip housing as described herein, e.g., to rotate and/or translationally oscillate. In some variations, the needle electrodes may be connected to a linkage that is configured to connect to the driver. The removable treatment tip may have a tip housing 114 (treatment tip housing) enclosing the needle electrode(s) and the linkage (not visible in FIGS. 1A-1C) and may also include a connector 131 for connecting the tip housing to the holder housing 111.

The driver (e.g. motor, not shown) may be controlled by a manual or automatic control 109 (e.g., button, switch, foot switch, finger button, toggle, etc.) on the apparatus to move the one or more needle electrodes. The control may in turn connect to a controller 121 which may be internal to the holder housing or separate (as shown in FIG. 1A). The same control may control the application of electrical energy through the one or more electrodes. In some variations a separate control for moving (e.g., rotating and/or mechanically oscillating) the electrodes and for applying energy may be included; in some variations although a separate movement control (e.g., rotating and/or mechanically oscillating the electrodes) may be included, the control for applying electrical energy may also trigger movement of the electrodes.

In the system shown in FIG. 1A, the treatment tip or treatment tip device 105 may be configured as a disposable tip. The treatment tip may include the needle electrodes, a frame supporting the needle electrodes while allowing them to move in rotation and/or oscillation (e.g., vibration) and a mechanical coupler for coupling the electrode(s) to the reusable driver in the re-usable portion of the electrical applicator (e.g., the base or holder portion 115). The treatment tip may include linkage coupler that may connect the linkage to the driver on the reusable holder; the linkage coupler may mate with a connector on the re-usable holder or may directly connect to the driver within the holder. Typically, a linkage translates the movement of the driver into rotation and/or translational oscillation (or in some variations non-oscillatory translation) of the one or more needle electrodes. This is illustrated in greater detail below in reference to FIGS. 2A-10. In FIG. 1A, the system shown also includes a power source 123, which may be a battery and/or power management circuitry (e.g., for using wall line power). The controller 121 may be included in the separate unit or may be included within the handle portion 115.

In general, the distal tip may include the one or more electrodes which may be configured in any appropriate manner for penetrating and making electrical contact with the tissue. In the example shown in FIGS. 1A-1C the tip (distal tip) includes a needle housing 143 into which the needle electrodes 107 may be retracted, as shown in FIG. 1B, and extended, as shown in FIG. 1C. In this example, FIG. 1B illustrates an example of a distal end of a retractable treatment tip device including an insulating cover through which electrodes (e.g., needle electrodes) may be extended, as shown in FIG. 1C. In FIG. 1B the soft insulating cover 117 may be smooth or may have openings through it. The needle housing 143 may be retracted by pushing against it with sufficient force to overcome a bias from, e.g., a spring within the device, so that the needle electrodes 107 extend out of the insulating cover 117, as shown in FIG. 1C. Alternatively, the needle electrodes may be extended out while the needle housing 143 remains in a fixed position. In some variations, the needle electrodes are not retracted or retractable into a needle housing but remain extended at all times.

In general, there are many ways that the one or more needle may be moved within the tissue to prevent arcing. For example, FIGS. 2A-2F illustrate various types of movement for a set of treatment needle electrodes 207. Each of these needle electrodes is coupled to a needle frame 210. The needle frame may form part of a linkage. FIGS. 2A-2F show possible degrees of freedom about which the needle electrode or array of needle electrodes can be rotated or translationally oscillated (e.g., vibrated). In general, the translations movements (including oscillations) may refer to movement in very small increments, e.g., back and forth, rapidly. In some variations the needle electrodes may be oscillated by flexing them, which may cause displacement of the needle electrodes, as illustrated below in reference to FIG. 2F.

Figure 2F:
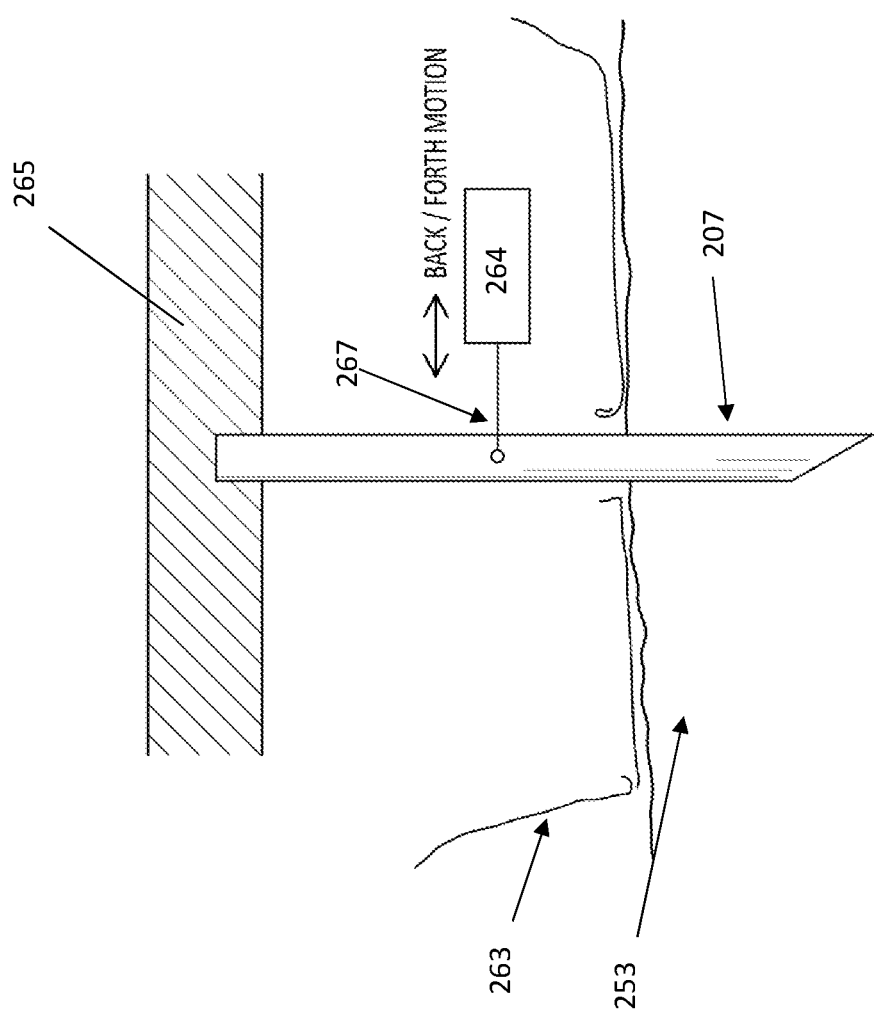

In FIG. 2A, the needle electrodes are shown oscillating in a yaw axis, e.g., rotating 221 the needle frame about the axis of the shaft 223. The shaft 223 and/or the frame 210 may be part of a linkage that is coupled between the needle electrodes 207 and the driver (not shown in FIGS. 2A-2F). The driver may oscillate or a portion of the linkage may translate movement of the driver into oscillatory movement. In FIG. 2A, the distance traveled by the individual needle electrodes may be small and may be different between different electrodes. In this example, needle electrodes that are further from the axis of rotation (through the shaft 223) will translate further than those closer to the axis of rotation. Any appropriate amount of movement may be used, as described above. For example, in FIG. 2A, the shaft may oscillate by just a few degrees (e.g., through an arc of less than 5 degrees, less than 4 degrees, less than 3 degrees, less than 2 degrees, less than 1 degree, less than 0.5 degrees, less than 0.3 degrees, etc.).

FIG. 2B is another example of a set of needle electrodes that are configured to oscillate, shown oscillating in the roll axis 231. The shaft 223 may be divided into a pair of oscillating piston members (or a single off-center piston member) that oscillates the needle frame 210 in a rocking motion. As mentioned for FIG. 2A, the amount of movement may be very small. For example, the rotation/rocking motion may be less than 5 degrees, less than 4 degrees, less than 3 degrees, less than 2 degrees, less than 1 degree, less than 0.5 degrees, less than 0.3 degrees, etc.). The absolute distance translated by the needle electrodes as they oscillate may be set by the length of the needle electrodes and the spacing from the axis of rotation 230 (the roll axis), but may be, e.g., less than about 4 mm, less than about 3 mm, less than about 2 mm, less than about 1 mm, less than about 0.8 mm, less than about 0.6 mm, less than about 0.5 mm, less than about 0.3 mm, less than about 0.1 mm, less than about 0.05 mm, etc.). In this example, the oscillation of the needle electrodes may follow an arc around the axis of rotation. In this example the shaft (e.g., piston(s)) and needle frame may be configured as a linkage that translates movement of a driver into oscillatory movement of the needle electrodes.

FIG. 2C is another example of a set of needle electrodes 207 that are coupled to a frame 210 and shaft 223. The shaft may be part of a driver or may be coupled to a driver so the frame and connected electrodes are moved up and down 241, in the long axis of the shaft, as shown. In this example, the driver (not shown) drives the oscillating up and down motion of the shaft and therefore the rigidly attached frame and needle electrodes. The oscillation of the shaft in this example directly corresponds to the movement of the needle electrodes (in other examples, mechanical movement multipliers or movement reducers/dividers may be used, e.g., such as gears, etc., which may be part of a linkage between the electrode(s) and the driver). The oscillation of the needle electrodes may be generally in-and-out (e.g., in the long axis of the needle electrodes), parallel with the long axis of the shaft.

FIG. 2D illustrates an example of a set of needle electrodes moving in two directions (e.g., left/right 251 and forward/backwards 261). Thus, the needle electrodes may vibrate or oscillate in more than one direction either simultaneously or sequentially.

Any oscillating movements may be used to move the electrodes within the tissue, including combinations of directions of movements (e.g., combinations of yaw, roll, pitch, up/down, in/out, left/right, forward/backwards, etc.) including any combination of translational movement and rotation. In general, the position of the electrode may move relative to the tissue being treated in an oscillatory or vibrational manner so that the portion of the electrode adjacent to a particular portion of the tissue is changing over time, caused by the movement of the electrode relative to the tissue.

For example, FIG. 2E illustrate an example in which each needle electrode 207 is rotated (spun in one direction or oscillating) 271 about its long axis. In FIG. 2E the bottom of the frame 210 holding the needle electrodes 207 is shown. The frame may include a housing and may be part of a treatment tip housing or device housing. Each needle electrode may be rotated together or separately and/or may be rotated with different rates and/or directions. For example, adjacent needle electrodes may be rotated in different directions. As mentioned, the rotation may be one-directional (e.g., clockwise) or it may alternate or oscillate in different directions (clockwise/counterclockwise). The rate of rotation may be between 0.01 Hz and 10 kHz (e.g., between 0.1 Hz and 1 kHz, between 0.1 Hz and 200 Hz, etc., in rotations/second).

FIG. 2F illustrate an example in which a needle that is shown within the tissue 253 is flexed by the back-and-forth movement of a driver 264. The needle is shown partially enclosed within a tip housing 263 and coupled to a frame 265. The movement of the driver, which may be directly coupled to the needle(s) or may be coupled through a linkage 267, may move (e.g., oscillate) the needle within the tissue. The needle may flex (e.g. bend) slightly during this motion. In some variations the needle is fixed proximally (e.g., to a frame) and constrained more distally, e.g., constrained in the back-and-forth direction of motion, but allowed to slide (e.g., move up/down). This may allow the needle to flex in the tissue, so that the side-to-side motion imparted by the driver results in a flexing (bending, up/down) motion in the tissue. This distance translated may be small, but may prevent arcing.

FIGS. 3-10 illustrate other examples of portions of the apparatuses described herein including the one or more electrodes (shown for convenience here as needle electrodes) and a driver; a linkage between the driver and the electrodes are also shown. These figures illustrate different embodiments of achieving movement of the electrode(s) relative to the tissue, but it should be understood that other variations may be used, or any combination or sub-combination of these.

Figure 3:
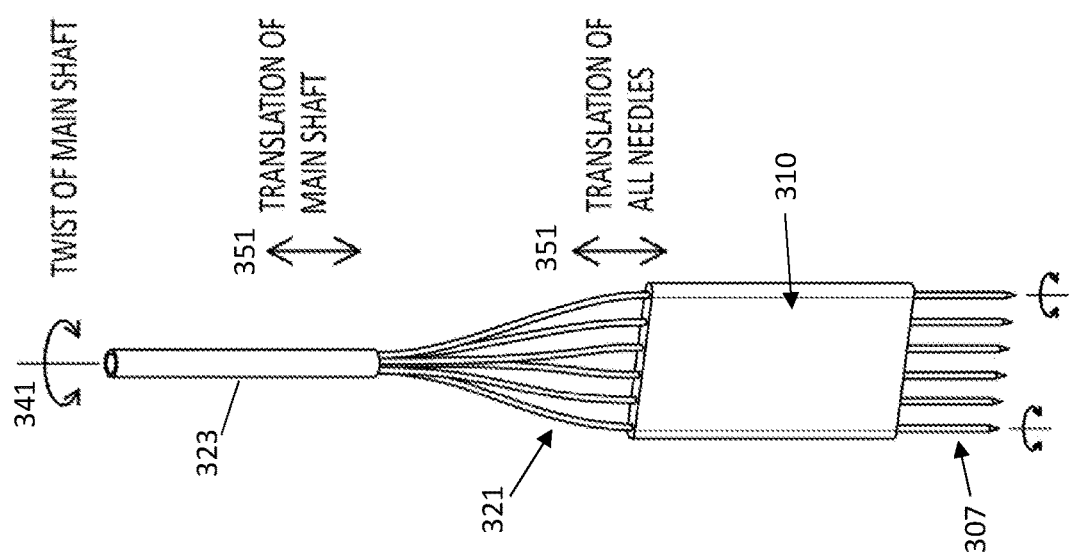
FIG. 3 is an example of an assembly for moving (e.g., rotating and/or oscillating) an array of needle electrodes by rotating a linkage shaft.

FIG. 3 shows an example of a mechanism for rotating an array of needle electrodes 307 by rotating a main shaft 323. In this example, the main shaft 323 either divides into a plurality of sub-shafts or is fixedly attached to the outside of these sub-shafts 321. The sub-shafts may be continuous with the needle electrodes or they may each couple to a needle electrode 307. In FIG. 3, the needle electrodes 307 and sub-shafts 321 are held by a needle electrode frame 310 but may rotate within the needle electrode frame. This configuration may be moved, oscillated, or vibrated in multiple different ways. For example, the needle electrodes may be rotated about their individual long axes in the tissue by twisting the main shaft 323 as shown by arrow 341. Alternatively or additionally, the set of needle electrodes may be collectively moved up and down within the tissue by translating the entire assembly up/down 351. In this example, the needle electrodes may also be coupled to an electrical source (e.g., for applying pulsed electrical energy) through the sub-shafts 321. Thus, the sub-shafts may be wires or the like.

Figure 4:
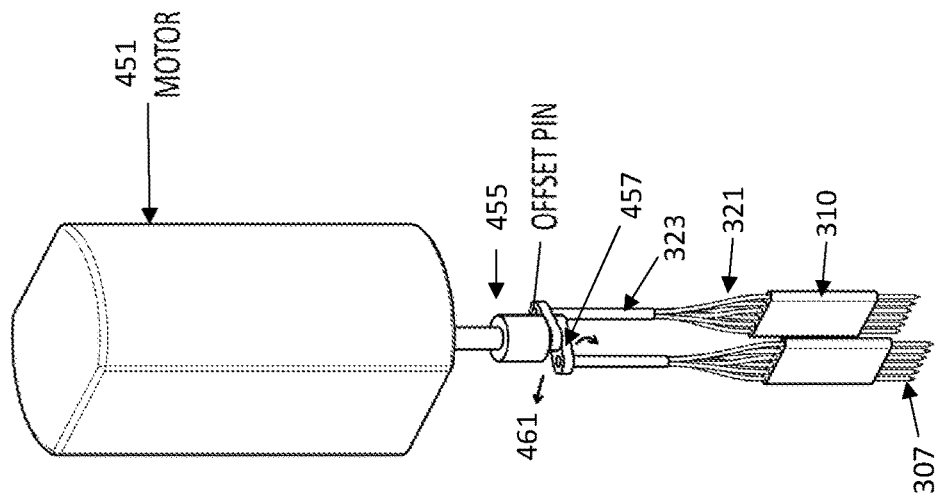
FIGS. 4 and 5 show another example of an assembly for moving an array of needle electrodes.
Figure 5:
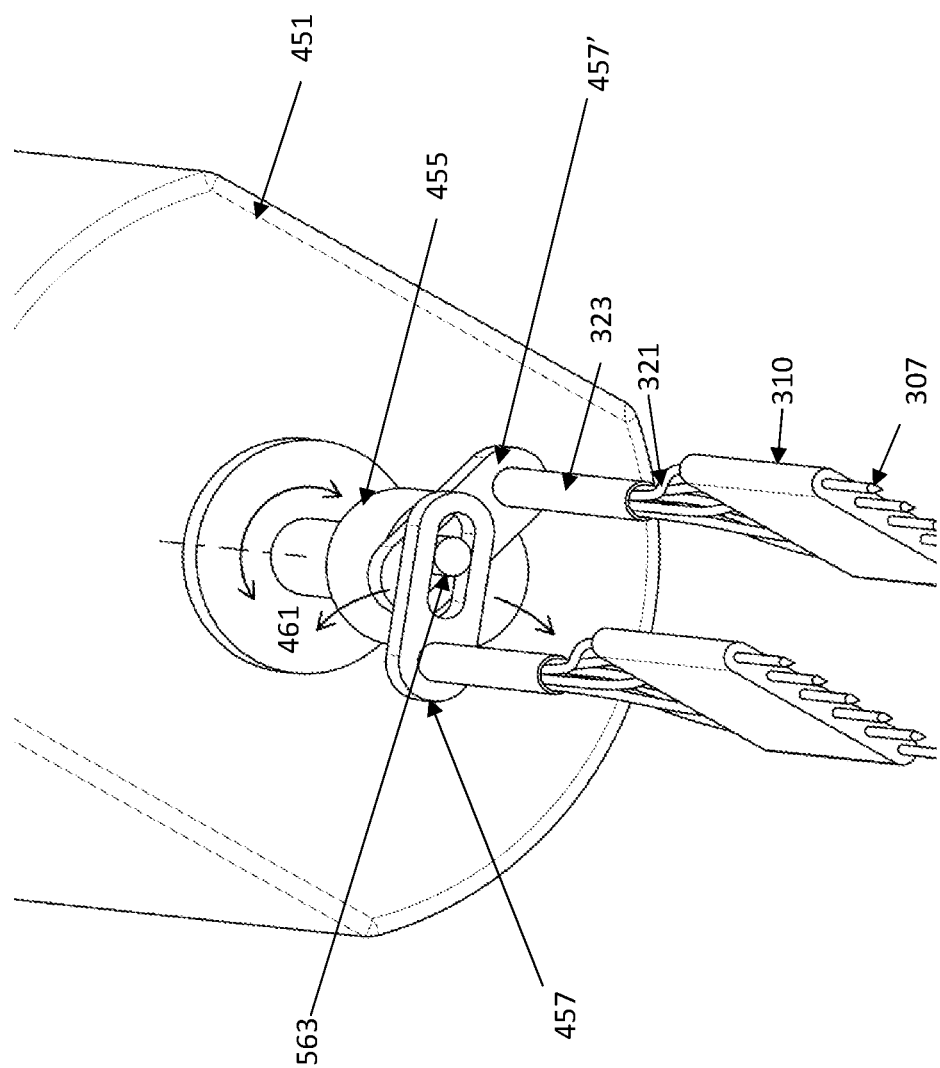

FIGS. 4 and 5 illustrate another example of a method of oscillating multiple arrays of needle electrodes with a single driver (e.g., motor) 451 using a pin 563 offset from the motor axis and a linkage connected to the main needle shaft, as shown in FIG. 5. In FIG. 4, the offset pin is on the rotating axle 455. Rotational motion from the driver may be changed to an oscillation motion (back and forth 461) by the linkage 457 being driven by the offset pin 563. FIG. 5 shows a bottom view of the assembly shown in FIG. 4, showing the pin 563 that is offset from the central axis of the rotating shaft or axle 455 of the motor 451. The pin rotation is translated into oscillating back-and-forth motion by the linkage 457, 457'. This back-and-forth motion 461 then translates the main shafts 323 of each linkage, and causes them to move and rotate each needle electrode back and forth (e.g., clockwise then counterclockwise), particularly when the holders (e.g., needle electrode frame holding the electrodes) 310 are held fixed while the needle electrodes 307 are allowed to move. This assembly may also include a housing (not shown) and a frame or mount for holding the needle electrodes, electrode frame, motor, etc. in position while allowing the oscillatory motion of the needle electrodes.

Figure 6:
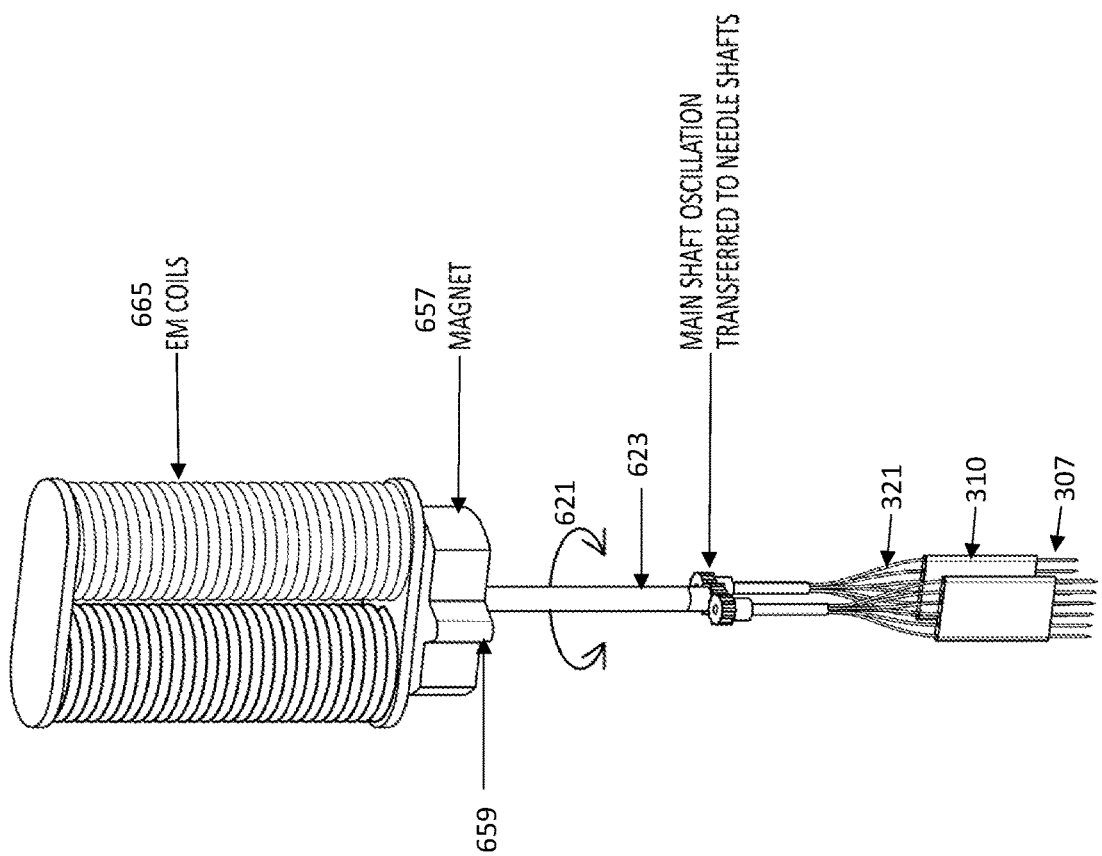
FIG. 6 is another example of an assembly for moving a plurality of needle electrodes that is driven by a pair of EM coils.

FIG. 6 illustrates another example of an apparatus for vibrating electrodes such as needle electrodes. In FIG. 6, the driver is a pair of EM coils 665 that may be alternately activated to cause oscillation of the main shaft 623 about its axis as indicated by arrows 621. In this example, the electromagnetic coils 665 may be alternately activated to cause the magnet 657 below to rotate one way and then the other. This rotation can be transferred to the individual arrays with a linkage (e.g., gears) and/or other structures. The magnet 657 is rotatably coupled near the magnetic field driven by the EM coils, and may include a stop 659 to limit rotation.

Figure 7:
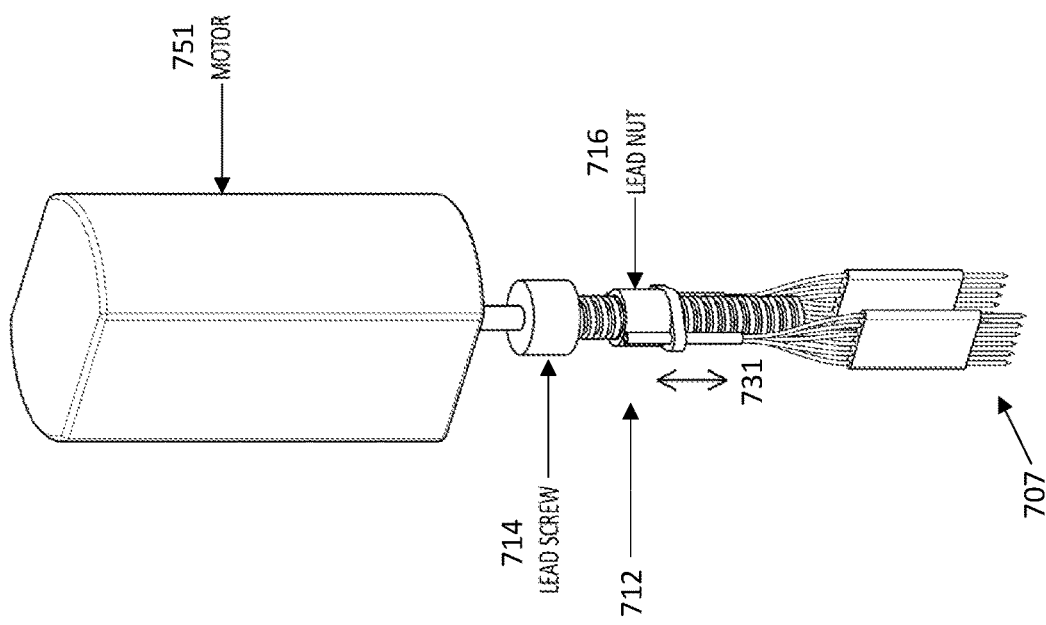
FIG. 7 shows an example of an assembly for moving a plurality of needle electrodes to advance and retract into the tissue.

FIG. 7 illustrates another example of an assembly (e.g., apparatus) including a motor 751 and a linkage 712 that is configured as a lead screw 714 and lead nut 716 that may be used to cause translation 731 of the main shafts connected to needle electrodes 707 so that the needle electrodes may be advanced and retracted when actuating the driver (motor). This could be used to slowly advance the needle electrodes during a cycle and/or advance/retract the needle electrodes to get axial vibration.

Figure 8A:
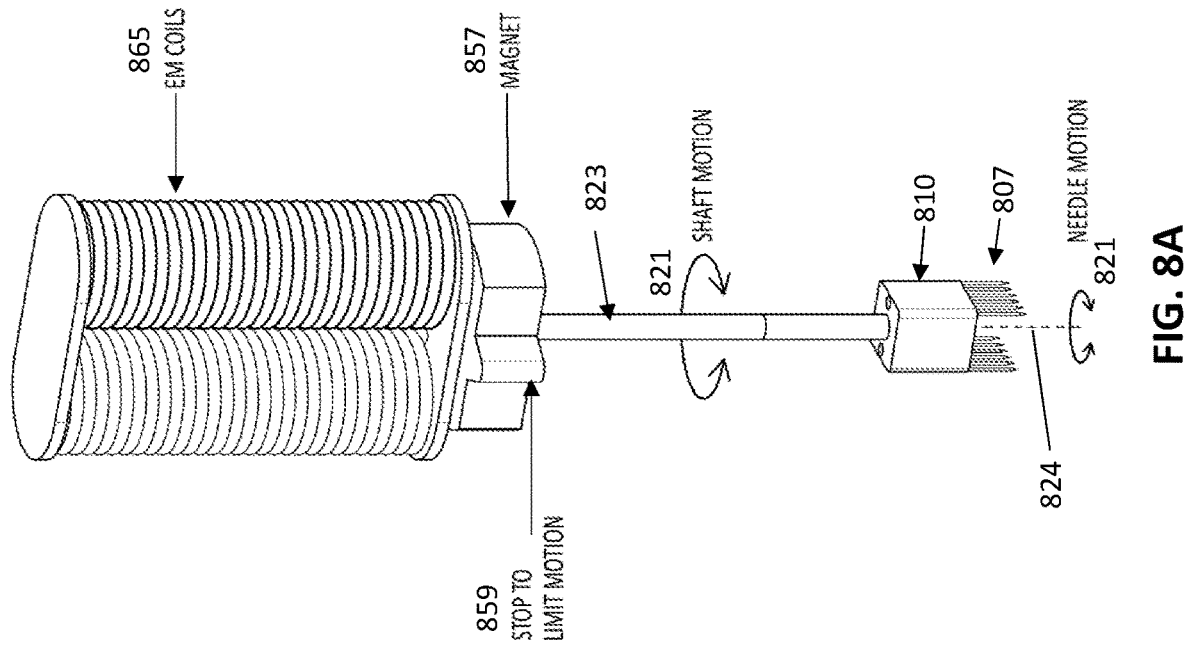
FIG. 8A is an example of an assembly for moving a plurality of needle electrodes.

FIG. 8A illustrates another example of an apparatus similar to that shown in FIG. 6. In FIG. 8A a solid array of needle electrodes 807 is vibrated about a center axis. In this example, each needle electrode is fixed relative to the other needle electrodes and connected to a shaft 823 that connects to a magnet 857 so that the entire block of needle electrodes moves together. A block frame 810 is used to hold the needle electrodes. The magnet 857 portion of the driver is moved by the changing electromagnetic field from the EM coils 865. A stop 859 is also included to limit the motion of the magnet and therefore oscillation of the electrodes. In this variation, the needle electrodes are oscillated 821 about the central axis 824.

Figure 8B:
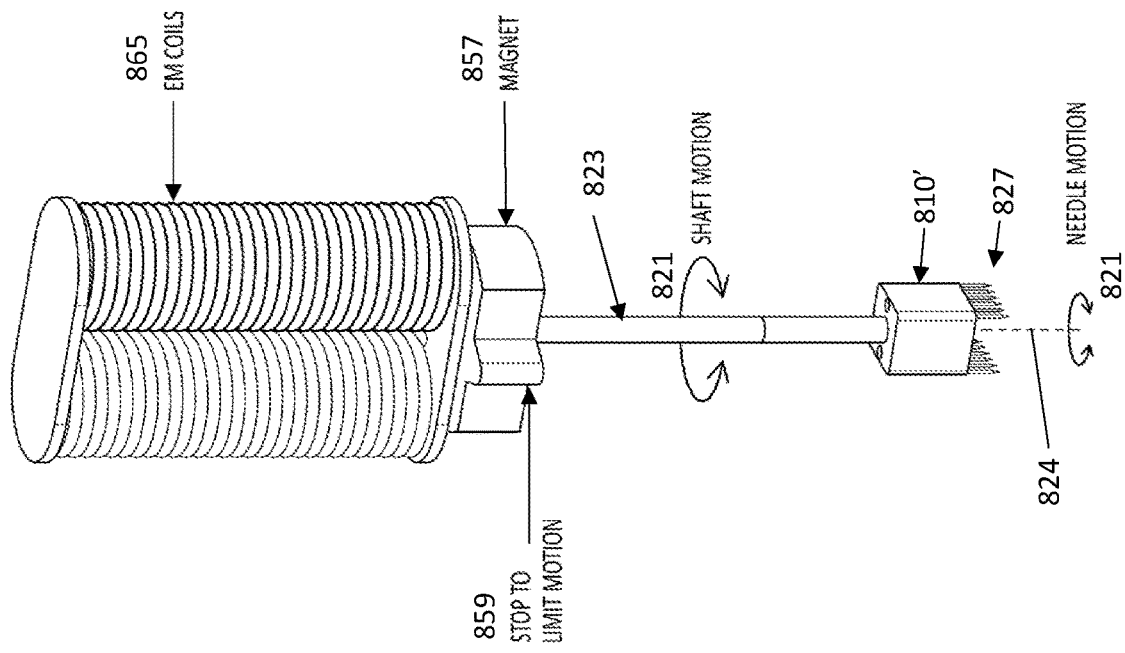
FIG. 8B is an example of an assembly for moving a plurality of knife electrodes, similar to that shown in FIG. 8A.

FIG. 8B is similar to the variation shown in FIG. 8A, but using knife electrodes 827 rather than needle electrodes. In FIG. 8B, a pair of knife (also referred to as blade) electrodes 827 are vibrated (oscillated) about a center axis. In this example, each knife electrode is fixed relative to the other needle electrodes and connected to a shaft 823 that connects to a magnet 857 so that the entire block with the knife electrodes moves together. The knife electrodes may be retracted into the housing completely or partially; alternatively the housing may extend/retract over the knife electrodes partially or completely. A block frame 810' is used to hold the needle electrodes. As in FIG. 8A, the magnet 857 portion of the driver is moved by the changing electromagnetic field from the EM coils 865, and a stop 859 is also included to limit the motion of the magnet and therefore oscillation of the electrodes. In this variation, the knife electrodes are oscillated 821 about the central axis 824. The knife electrodes may have a sharp distal edge for cutting through/into the tissue. Other penetrating electrodes may be used in place of any of the variations described herein, including comb-electrodes, fork electrodes (e.g., having one or more tines for penetrating the tissue), or the like. Although the configuration shown in FIG. 8B is shown oscillating about the axis 823, in some variations, the knife electrodes may be moved up/down into/out of the tissue and/or may be moved back/forth (e.g., in the long axis of the blade).

FIGS. 9 and 10 illustrate an example of a driver configured as a solenoid that may be used to move the needle electrodes up/down slightly in the tissue. In the example shown in FIG. 9, as in FIG. 8A, a solid array of needle electrodes 907, which is held by a needle frame 910, may be vibrated in/out 931 using a solenoid 965 and spring (not shown) to push/pull on the shaft 923. For example, the shaft may include a magnet that is moved up/down at the driving frequency by the field of the solenoid; the spring may limit the motion of the shaft. In any of these examples a return spring (not shown) may be included to aid or provide a return force so the solenoid pulls or pushes the needles in one or more direction, and the spring returns them, or assists in moving them (in conjunction with the solenoid).

FIG. 10 shows a configuration of an assembly in which the solid array of needle electrodes 901 is coupled to a linkage 1005 that translates the push/pull motion 931 of the shaft 923 from the solenoid 965 into a rocking (e.g., roll 1031) motion, rocking the needle electrodes back and forth about a horizontal pivot 1025.

Figure 11:
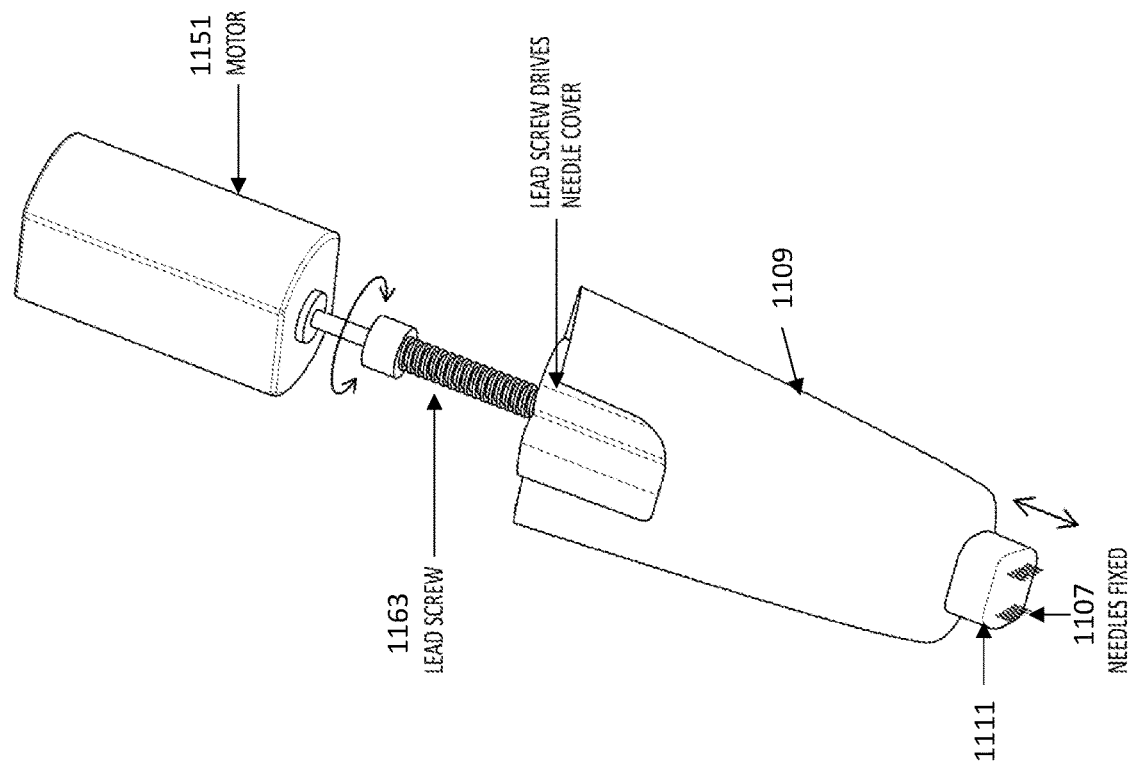
FIG. 11 illustrates an example of another assembly partially enclosed within a housing. In this variation, the housing may be driven relative to the electrodes.

FIG. 11 illustrates another example of an assembly that may be at least partially enclosed within a tip housing 1109. In this example, the housing is moved (e.g., translational oscillation) by a lead screw 1163 arrangement that is driven by a driver (e.g., motor 1151) and may extend and/or retract the needle electrodes 1107 into or out of the needle housing 1111, to expose or enclose the needle electrodes. In some variations, the needle electrodes may be moved by the driver (or by the linkage and driver), to oscillate relative to the tissue. Alternatively, the needle housing 1111 may be moved by the driver (e.g., or by the linkage and driver) to change the exposed length of the needle electrodes from the needle housing; this may also be used to move the needle electrodes relative to the tissue, for example, when the needle housing is held against the tissue, the apparatus may move in and out relative to the tip face of the needle housing into and out of the tissue.

In some variations of the apparatuses and methods described herein, rather than or in addition to moving the electrodes and/or tip housing, the tissue itself maybe moved (vibrated, oscillated, etc.) slightly during application of the energy, which may also reduce or eliminate arcing.

Figure 12:
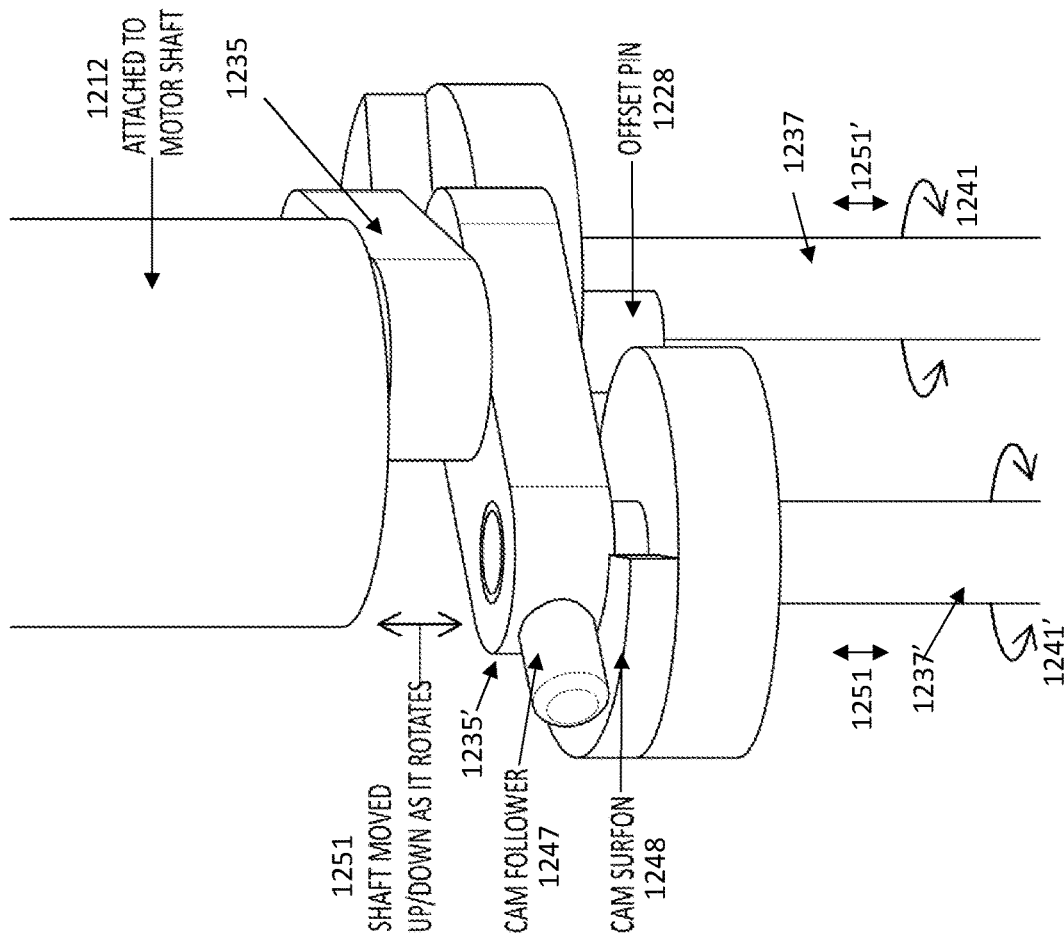
FIG. 12 is an example of a linkage portion of an assembly to move one or more electrodes in more than one type of motion.

FIG. 12 is another example of a linkage portion of an assembly that may connect to a driver (motor, not shown) to move the electrodes in more than one type of motion. In FIG. 12, the motor drives a motor shaft 1212 and rotates a pin that is off-center (offset) on the face of the shaft (offset pin 1228) and that moves each of two hinged linkages 1235, 1235'. Two branches of the hinged linkage are connected to the pin, so that rotation from the motor shaft is translated into an oscillating motion of each of two hinged linkages (e.g., rotating partially about the shaft axes). Translation shafts 1237, 1237' are connected to each hinged linkage and each is moved in the oscillating pattern 1241, 1241' as the hinged linkages move. Furthermore, each hinged linkage has a cam follower 1247 that rides on a cam surface 1248 so that as the linkage gears move across the cam surface the height of the translation shaft may go up and down 1251, 1251'. The electrodes (e.g. needle electrodes) may be coupled to the ends of the translation shafts. Thus, the single rotational motion of the driver may be translated into a variety of oscillating movements in the electrodes.

Figure 13:
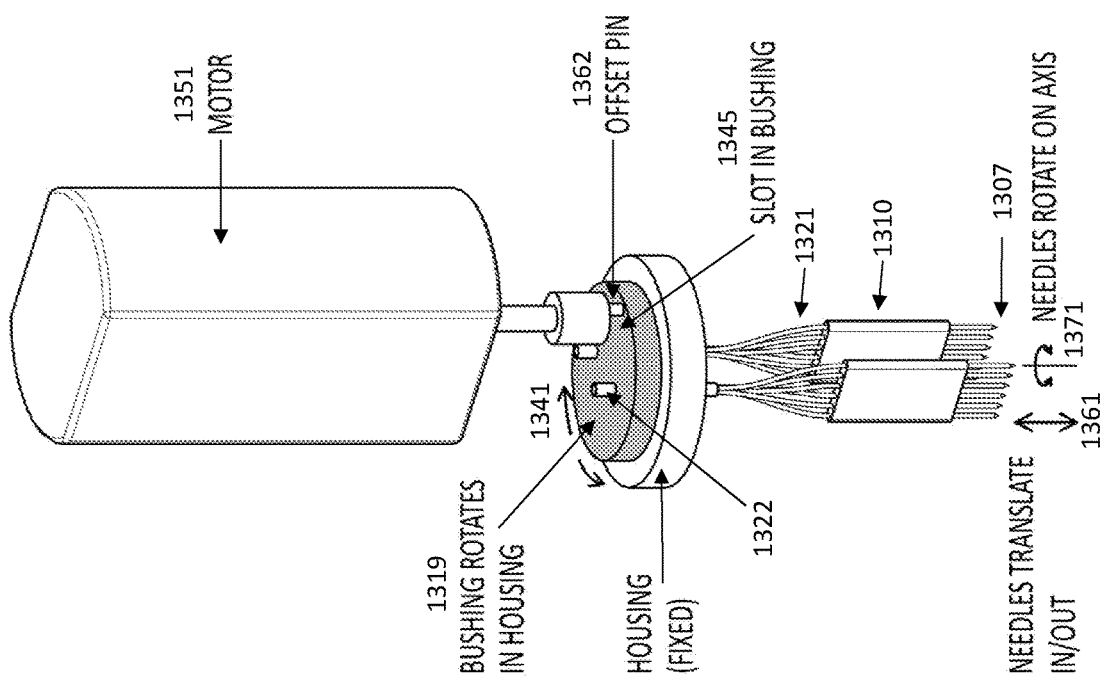
FIG. 13 shows an example of an assembly for moving a plurality of needle electrodes in more than one type of motion.

FIG. 13 is another example of an assembly that moves needle electrodes 1307 both in and out slightly as well as in rotation. In FIG. 13, the driver (motor 1351) rotates a motor shaft to drive rotation of an offset pin 1362 that is engaged with a bushing 1319 that translates the rotation of the offset pin into alternating oscillation 1341 of the bushing 1319. The offset pin may be held in a slot 1345 in the bushing. As described above in FIG. 3, a group of needle electrodes may be coupled to a plurality of sub-shafts 1321 that are connected to (or form) a main shaft. The main shaft 1322 may be connected to the oscillating bushing. If the main shaft, and therefore one end of the sub-shafts, are fixedly connected to the oscillating bushing, as it oscillates, the flexible sub-shafts will flex and will move the needle electrodes (which may be slideably held within an electrode frame 1310) both up and down as shown by arrows 1361 and will also rotate the individual needle electrodes slightly as shown by 1371. In this example, the needles will translate up and down 1361, so that needle electrodes at one end of the same row of needle electrodes will move up while the needle electrodes at the opposite end of the same row moves down. Note that if the main shaft is not fixed to the oscillating bushing, but is allowed to rotate, while being driven side-to-side by the bushing, the needle electrodes may just translate up and down but not rotate.

Figure 15:
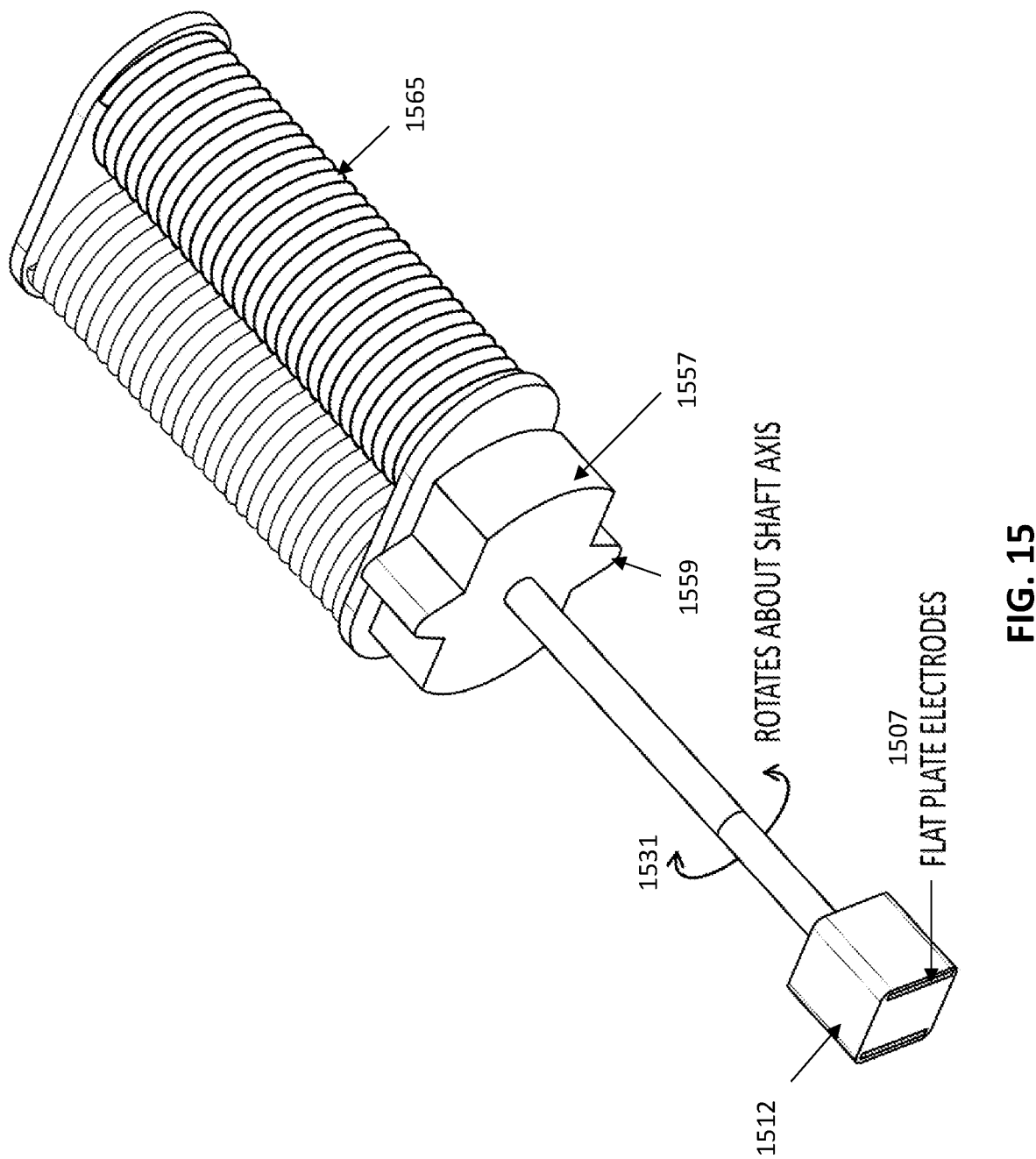
FIG. 15 is an example of an assembly for moving plate electrodes (configured as a pair of elongate flat plates on an outer surface of the apparatus) as described herein.

FIG. 15 illustrates an example of an assembly for moving an electrode. The driver in this example is similar to that shown in FIGS. 8A-8B, however the electrode is a surface electrode (shown configured as a flat plate electrode). In FIG. 15, two plate electrodes 1507 extend along the surface of the housing 1512, and the housing and plate electrodes may be oscillated in rotation about a center axis of the shaft 1531. Alternatively in some variations, the housing may remain fixed while just the surface electrodes move relative to the housing. In this example, each electrode 1507 extends in a line, but may be any appropriate shape, including circular, oval, elongate, X-shaped, T-shaped, etc. The electrodes may be independently or collectively moved. In FIG. 15, the housing and electrodes are connected to the shaft 1531 which also connects to a magnet 1557 so that the electrodes moves together. A frame (not shown) may hold the plate electrodes in the housing, particularly in variations in which the apparatus moves together. The magnet 1557 portion of the driver is moved by the changing electromagnetic field from the EM coils 1565. A stop 1559 is also included to limit the motion of the magnet and therefore limit oscillation of the electrodes.

Figure 16:
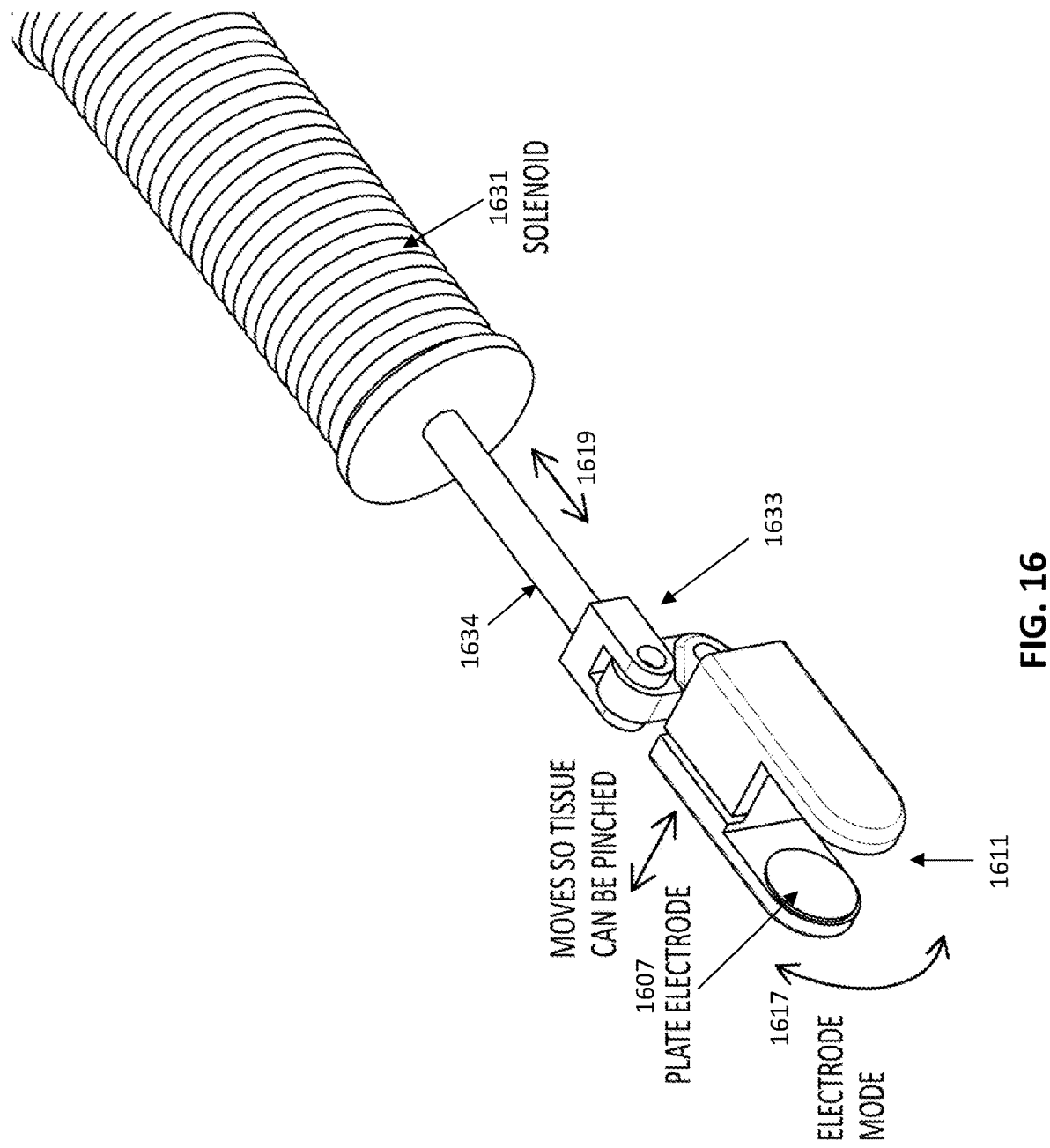
FIG. 16 shows another variation of an assembly for moving an electrode, shown configured as a clamping electrode (a plate electrode) that may be held on either side of a tissue and operated as described herein.

FIG. 16 is another example of an assembly for moving an electrode. In this example, the electrode is configured as a surface plate electrode (or a pair of surface plate electrodes) 1607 that are positioned on opposite sides of a pair of jaws 1611. The jaws may be fixed relative to each other or they may be opened and/or closed. The jaws may be configured as a clamp. For example, the jaws may be biased (e.g., by a spring) to close over a tissue. The jaws may be positioned on either side of a target tissue to be treated. During treatment (e.g., during application of the energy therapy, which may include the application of pulsed electrical energy or continuous electrical energy) the electrode(s) may be moved by the driver, shown as a solenoid 1631. The solenoid may drive the movement 1619 of the shaft 1634, which may be translated into a rocking (e.g., pitch) motion 1617 at the electrodes by the linkage 1633.

Any of the apparatuses described herein may be used as part of surgical procedure, including a minimally invasive surgical procedure. Any of the apparatuses described herein may be delivered or deployed through an endoscope, cannula, or the like. In particular, the apparatuses described in FIGS. 15 and 16 may be used internally by application through an endoscope. Thus, any of these apparatuses may be operated with (as part of a system) including an endoscope and/or may be integrated with an endoscope or other invasive tool. In operation, any of these devices may be inserted into a surgical incision and/or a port into a body region or body cavity. As mentioned above, although the apparatuses and methods described herein are directed towards insertable electrodes, the principles and features described herein may be adapted for external treatment, including skin surface and/or organ-surface treatment.

All of the assembly configurations described herein may also have a connection to a power source for applying energy to the tissue through the electrodes. The same energy source may be used to power the driver, or a separate energy source may be used (or both).

Any of the assemblies shown by example in FIGS. 2A-13 and 15-16 may be included as part of an apparatus such as a treatment tip device for delivery of electrical therapy. For example, the treatment tip may include the electrodes and linkage, and a housing and/or frame holding the needle electrodes and linkage so that the needle electrodes may move as described. In some variations the treatment tip may include a driver (e.g. motor, magnet, etc.). In other variations, the treatment tip does not include the driver (or all of the driver) but includes a coupler/connector for connecting to the driver. The driver may be divided between a removable treatment tip with the electrodes, and a reusable/durable tip holder. For example, a reusable durable tip holder may include one or more magnetic coils that may drive oscillation of a magnet coupled to the electrodes and/or to a linkage in a disposable tip. In some variations a piezoelectric driver may be included in the disposable tip. Any of the tip apparatuses described herein may include a power connector configured to electrically connect the one or more needle electrodes to a power source. In some variations, the drive is a shape-memory alloy (SMA) actuator.

In addition, all of the assemblies and apparatuses described herein could also be used to reduce tenting, for example, by moving the electrodes without applying energy when inserting into the tissue (e.g., through the tissue).

Figure 14:
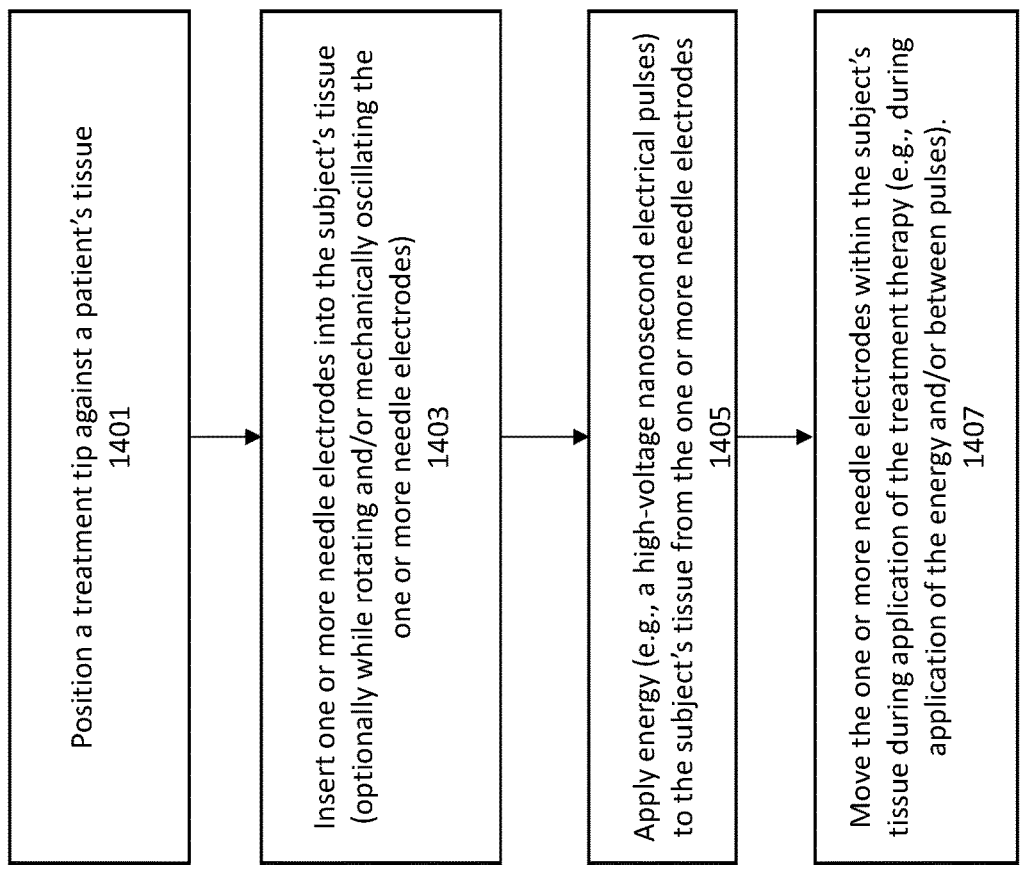
FIG. 14 illustrates one method of treating a tissue using an apparatus as described herein.

In use, any of the apparatuses described herein may be configured to be operated to prevent, reduce, or limit unintended modification of the tissue adjacent to the electrode, such as by arcing. For example, FIG. 14 illustrates an example of a method of applying an electrical therapy to a subject using any of the apparatuses described herein. In this example, the method may include inserting one or more needle electrodes into the subject's tissue to apply energy through the needle electrodes. Alternatively, other types of electrodes may be inserted, or optionally, these methods may be used after the electrodes have already been inserted into the tissue.

In variations in which the electrodes are to be inserted into the tissue, the apparatus, such as a system for delivery of electrical therapy, a device for delivery of electrical therapy, and/or a treatment tip as described above, may be first positioned against the tissue (step 1401). In some variations, the electrodes (e.g., needle electrodes) may be inserted while vibrating, moving, and/or rotating them (step 1403). As mentioned above, this may help prevent arcing due to tenting, for example.

Once in position, in step 1405 the energy may be applied to the subject's tissue through the electrodes. In step 1407 one or more electrodes may be moved (e.g., rotated and/or translationally oscillated) slightly relative to the tissue to be treated during application of a treatment therapy (e.g., either during application of the energy or between the pulses). Any appropriate energy may be applied, including high-voltage, pulsed energy (e.g., high-voltage nanosecond electrical pulses). Once treatment is completed, the electrodes may be removed.

Any of the methods (including user interfaces) described herein may be implemented as software, hardware or firmware, and may be described as a non-transitory computer-readable storage medium storing a set of instructions capable of being executed by a processor (e.g., computer, tablet, smartphone, etc.), that when executed by the processor causes the processor to control performance or perform any of the steps, including but not limited to: displaying, communicating with the user, analyzing, modifying parameters (including timing, frequency, intensity, etc.), determining, alerting, or the like.

Although the exemplary apparatus and method discussed above moves the electrodes when applying energy to the tissue, in any of the variations described herein, the apparatus may be configured to move when applying an energy therapy (e.g., when applying energy through the electrodes) when triggered by detection of a signal, such as detection of an electrical property of the tissue. For example, the method and apparatus described herein may be configured to move the one or more electrodes when the apparatus detects a change in the impedance at the electrode that exceeds a threshold. A change in impedance at the one or more electrodes may indicate a higher likelihood of arcing. In particular, in some variations the rate of change of impedance of the tissue may indicate an increased likelihood of arcing and may therefore be used as a trigger to activate movement of the one or more electrodes before and/or during the application of electrical energy from the one or more electrodes.

One or more electrical properties of the applied energy and/or tissue may be measured in any of the apparatuses described herein, and may be used to adjust the applied energy, including (but not limited to) adjusting the movement (e.g., rotation, translation oscillation and/or non-oscillatory translation) of the one or more electrodes. For example, the impedance of the tissue may be detected and used to adjust the treatment, an in particular, the movement and/or applied energy. Alternatively the voltage, current, applied energy or applied power may be directly measured and used to adjust the treatment. For example, one or more of the voltage, current, applied energy, impedance or power applied may be detected and/or measured and changes in one or more of these parameters may be used to adjust the applied energy or power (e.g., voltage, pulse width, pulse repetition rate/frequency, number of pulses, etc.). Thus, electrical impedance may be estimated from other electrical properties, or the other electrical properties may be directly used. For example, a change in measured impedance (e.g., magnitude, or rate of change) may be due to changes in tissue impedance; as current, voltage and electrical power are related (e.g., via Ohms Law) any of these parameters may be measured and adjustments made based on the changing measurements to reflect the changing impedance of the tissue during treatment.

In some variations, the tissue impedance (or other electrical properties) may be measured using the same electrode that is applying the energy, or a nearby (e.g., adjacent) electrode may be used. Tissue impedance may be measured before, during and/or after applying energy to the tissue. For example, a tissue impedance measurement circuit for one or more electrodes (e.g., for each electrode) may be included, and may be part of or connected to the controller. The measured tissue impedance may provide estimates of tissue impedance that may be used by the controller to control the application of energy and/or the movement of the one or more electrodes.

For example, any of these apparatuses may measure an electrical property, including tissue impedance, during pulsing. When the electrical property, such as impedance, changes by a predetermined amount, and/or at a predetermined rate of change, which may indicate that there is an increase susceptibility for arcing, the electrodes may be moved. The predetermined amount maybe determined empirically (e.g., by testing for arcing), and may be generic or may be tissue-specific. Once the electrical property changes relative to the predetermined amount the electrodes may be moved (rotated, oscillatory translation, non-oscillatory translation). The electrodes may be moved manually or automatically, including robotically, as described in greater detail below. For example, the change in impedance and/or the rate of change of impedance may be automatically detected by a processor or controller of the apparatuses of various examples, and the same or a different processor or controller may trigger and direct the movement of the one or more electrodes.

Alternatively or additionally, a change in an electrical property of the tissue such as an impedance drop may also trigger a change in energy parameters, such as a change in pulse parameters. For example, in response to an impedance change (or rate of change) the apparatus may adjust the voltage applied (e.g., lowering the voltage), adjust the pulse width (e.g., decreasing the pulse width), and/or decreasing the pulse intensity (increasing the duration between pulses), and/or pausing pulsing until the tissue impedance recovers below the threshold.

Figure 18A:
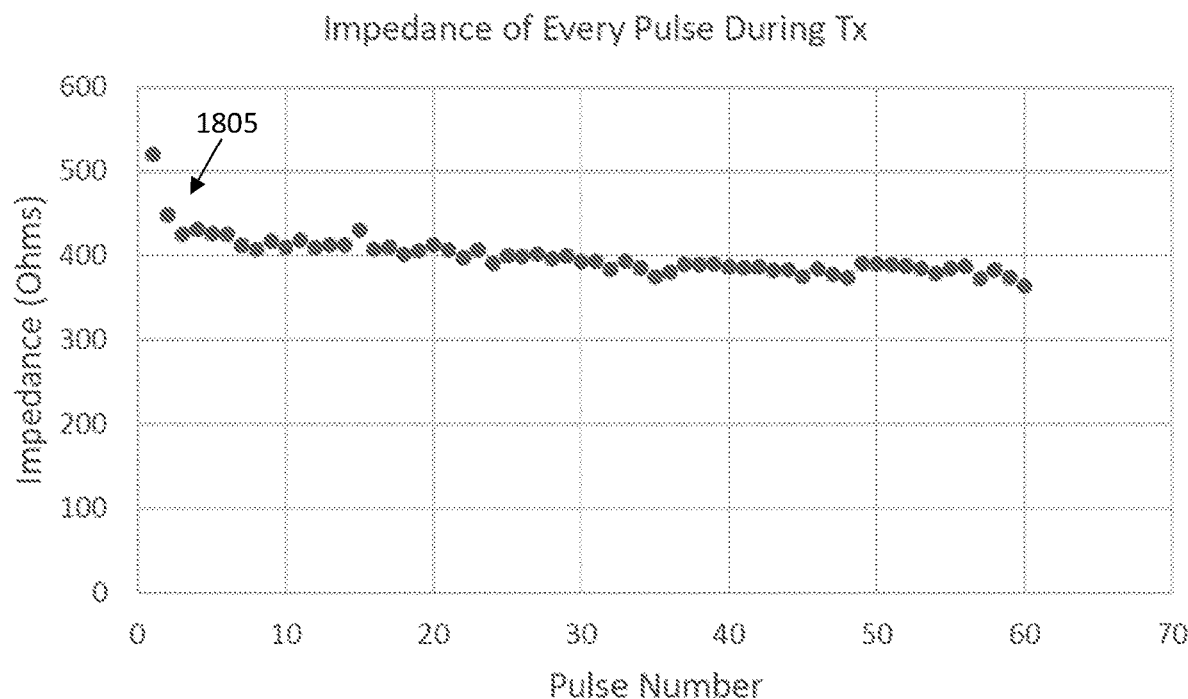
FIG. 18A is a graph showing the impedance of every pulse during an exemplary treatment transmission (Tx) having 60 pulses delivered to tissue; no arcing detected.
Figure 18B:
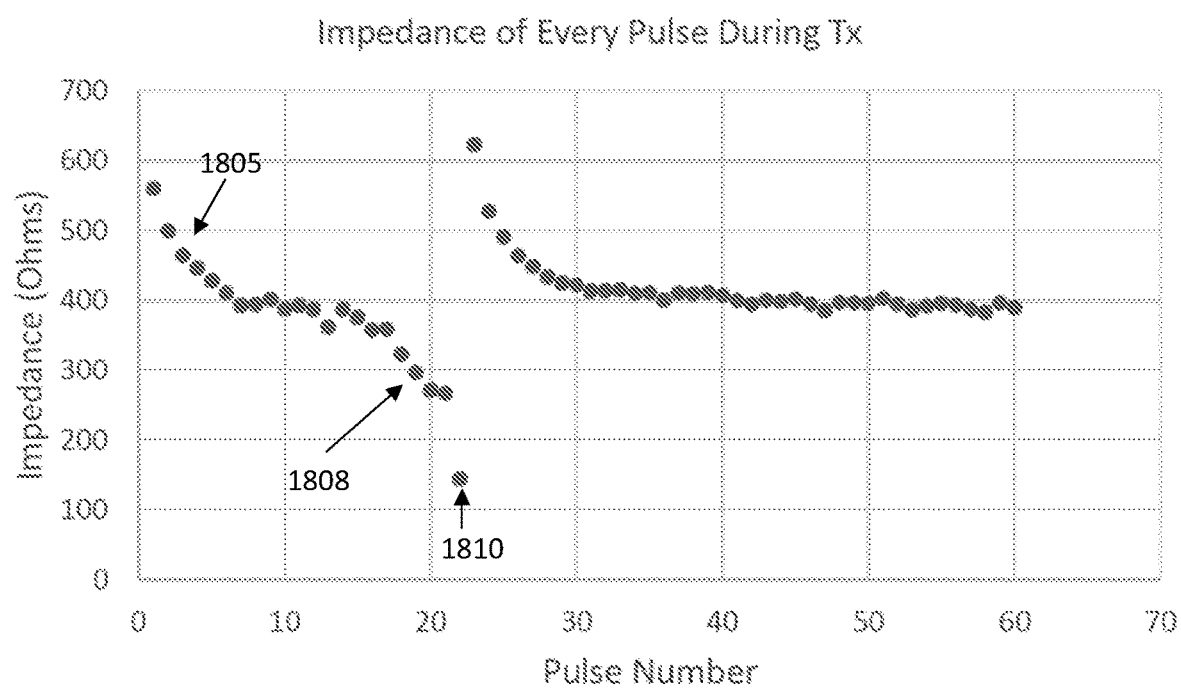
FIG. 18B is a graph showing the impedance of every pulse during another exemplary treatment having 60 pulses delivered to tissue, with arcing occurred.

FIGS. 18A and 18B illustrate the impedance measured for every pulse in a treatment of skin tissue using system for delivery of electrical therapy having one or more penetrating electrodes configured to deliver electrical energy to a tissue (similar graphs may be seen for surface electrodes). As mentioned above, other electrical properties of the, such as power, current and/or voltage applied may be detected and may show similar relationships to those shown in FIGS. 18A and 18B. Such electrical energy may be delivered, for example, at high voltage power to having a peak voltage of between 500 volts per centimeter (V/cm) and 500 kilovolts per centimeter (kV/cm) (e.g., greater than about 1 kV/cm, greater than about 5 kV/cm, greater than about 10 kV/cm, etc.), comprising sub-microsecond electrical pulses having a pulse width of between about 0.1 nanoseconds (ns) and 1000 nanoseconds (ns). In FIG. 18A, the treatment did not result in any arcing. In this example, the impedance starts off over 500 Ohms but then quickly drops off 1805, within the first 10 pulses, and levels off at approximately 400 Ohms. Sixty pulses are performed during the course of the treatment.

FIG. 18B shows an example of the impedance of every pulse during a treatment in which arcing occurred. The parameters used in FIG. 18B are otherwise identical to those of 18A. During the initial treatment period the impedance dropped rapidly 1805 from an initial impedance of greater than 500 Ohms to approximately 400 Ohms. However, after the 15$^{th}$ pulse the impedance again begins to drop rapidly 1808, immediately before arcing occurs at pulse 22 1810. In the example shown in FIG. 18B, the system paused the treatment when the arc was detected and the needles were moved slightly. When the treatment was started again (e.g., at pulse number 16 in FIG. 18B), the impedance started back at about 500 Ohms and then dropped back down to 400 Ohms for the remainder of the treatment, and no further arcing occurred. As in FIG. 18A, the measured impedance starts off above 500 Ohms and quickly drops. The impedance levels off at 400 Ohms. In FIGS. 18A and 18B, the magnitude of the impedance measured and the changes shown are a function of the electrode, pulse generator system, pulse shape, and tissue; although the actual magnitudes measured in any particular combination of these feature may be different, in general, the general principle illustrated (e.g., the sudden change in electrical properties) may be the same.

Thus, described herein are apparatuses (e.g., device, systems, etc.) including a processor configured to monitor the electrical characteristic (e.g., impedance) of each pulse delivered, and to adjust the treatment based on the electrical characteristic to prevent or reduce arcing. For example, an apparatus, including a processor of the apparatus, and method of treating may be configured to monitor the rate of change of the impedance, or a related electrical characteristic, of each pulse delivered and, after some initial period (e.g., of about 5, about 6, about 7 about 8, about 9, about 10, about 11, about 12, etc.) into the delivery of a train of pulses, if the rate of change of the electrical characteristic increases above a threshold (e.g., an impedance rate change threshold) and/or the electrical characteristic changes by more than a threshold percent (e.g., impedance percent change threshold), and/or the electrical characteristic changes by a threshold magnitude (e.g., an impedance magnitude change threshold) the pulse settings may be adjusted to prevent arcing. The examples of detection of a change in an electrical characteristic of the tissue and potential adjustment described above are examples; more involved statistical algorithms could be used to assess the changes in impedance or other measured parameters.

The adjustment may be one or more of: changing the inter-pulse timing of the pulses (e.g., increase or decreasing the frequency of the pulsing, such as increasing the time between pulses), changing the pulse magnitude (e.g., current and/or voltage magnitude of the pulses), and/or changing the pulse duration (e.g., increasing and/or decreasing the pulse duration).

For example, in some variations a system or method for treating a tissue using high voltage, sub-microsecond electrical pulses may be configured to monitor the rate of change of the impedance of individual pulses so that if, after the first x pulses (where x is 5, 6, 7, 8, 9, 10, etc.), the impedance of each pulse over time decreases at a rate that exceeds an impedance rate change threshold of about 1 Ohms/pulse (e.g., 5 Ohms/pulse, 10 Ohms/pulse, 25 Ohms/pulse, 50 Ohm/pulse, 100 Ohms/pulse, 500 Ohms/pulse, etc.), then the system or method may adjust the pulse settings to prevent arcing. In some variations, a system or method for treating a tissue using high voltage, sub-microsecond electrical pulses may be configured to monitor the percentage of change of the impedance of individual pulses compared to prior pulses, so that if, after the first x pulses (where x is 5, 6, 7, 8, 9, 10, etc.) the impedance of each pulse over time decreases by an impedance percent change threshold, such as a percentage of greater than 10% (e.g., 15%, 20%, 25%, 30%, 35%, 40%, 45%, 50%, 55%, etc.) for n consecutive pulses (where n is 2, 3, 4, 5, etc.), then the system or method may adjust the pulse settings to prevent, reduce or minimize arcing. In any of these variations x may be chosen manually or automatically, and or may be determined based on the treatment parameters.

Robotic Devices

Any of the above-mentioned devices and methods may be implemented with a fully or partially automated system, for example, computer-controlled or robotic system. For example, a device for applying electrical therapy may be operatively attached or coupled to a robotic arm. The robotic system may include one or more electrodes, a robotic arm, and at least one processor/controller. The system may include a separate driver mechanism driving the movement (e.g., rotation, translational oscillation, etc.) of the one or more electrodes. The movement of the electrical therapy device may be directed by a robotic arm, a driver mechanism of the robotic system, or combination of both. The at least one processor may control the movement of the robotic arm, the activation of the driver mechanism, or both. The same single processor may control all of the movements, or separate processors may direct the movement of the robotic arm and the driver mechanism. In some embodiments, the at least one processor (which may comprise one or a plurality of processors) may be operatively connected to a generator responsible for generating electrical pulses of the device for applying electrical therapy. The at least one processor may comprise instructions for implementing various methods described herein.

Figure 17:
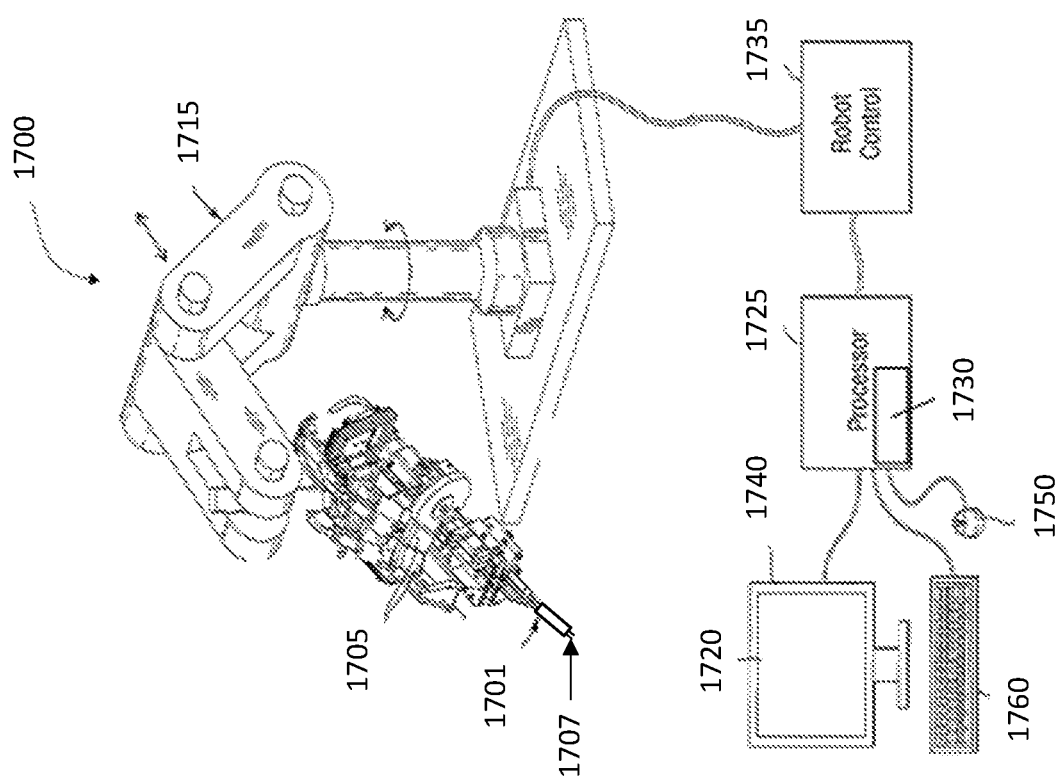
FIG. 17 illustrates an example of a robotic system for use with the devices and methods of the present disclosure.

FIG. 17 is a schematic perspective view of an example of a robotic system 1700 for delivering an electrical therapy without arcing. The system 1700 in this example includes a robotic arm 1715 to which is coupled a device 1701 for delivery of electrical therapy. This device (which may be subsystem of the robotic system or may be a separate element held by the robotic arm) may include one or more needle electrodes 1707 configured to deliver electrical energy to a tissue, and a power connector configured to electrically connect the one or more needle electrodes to a power source.

Various motors and other movement devices may be incorporated to enable fine movements of the device 1701 for delivery of electrical therapy and/or for operating the tip of the tool (device) 1701 so that it may be moved in multiple directions. The robotic system 1700 in this example further includes at least one (and preferably two for stereo vision, or more) image acquisition device 1705 which may be mounted in a fixed position, or coupled (directly or indirectly) to a robotic arm 1715 or other controllable motion device.

In those examples where image acquisition device is used, the processor 1725 of FIG. 17 may comprises an image processor 1730 for processing images obtained from the image acquisition device 1705. The image processor 1730 may be a separate device or it may be incorporated as a part of the processor 1725. The processor 1725 may also instruct the movements of the robotic arm 1715, including the tool (device for delivery of electrical therapy) 1701, and act, for example, through a controller 1735 as schematically shown in FIG. 17. The controller 1735 may be operatively coupled to the robotic arm and configured to control the motion of the robotic arm, including the motion based on the images or data acquired by the image acquisition device. Alternatively, controller 1735 may be incorporated as a part of the processor 1725, so that all processing and controls of all movements of all the tools, the robotic arm and any other moveable parts of the assembly, including those based on the images or data acquired by the image acquisition device, are concentrated in one place. The system 1700 may further comprise a monitor 1740, mouse 1750 and keyboard 1760. A magnified image of the tissue can be shown on the imaging display or monitor 1740. In addition, the system 1700 may comprise other tools, devices and components useful in applying the electrical therapy. The system may further include an interface (not shown) adapted to receive an image data, various parts of the system allow an operator to monitor conditions and provide instructions, as needed. The processor 1725 may interact with the imaging device 1705 via the interface. The interface may include hardware ports, cables, leads, and other data transmission means, or it may comprise a computer program.

Some non-limiting examples of an image acquisition device 1705 shown in FIG. 17 include one or more cameras, such as any commercially available cameras. The image acquisition or imaging device may be held, for example, by a robotic arm, or by any other mechanism or means. Various image acquisition devices or a combination of several devices could be used with any of the embodiments of the systems and methods described herein. The image acquisition device 1705 may comprise a device that takes still images, it can also comprise a device capable of real time imaging (e.g., webcam capable of continuously streaming real time information), and/or it could also have a video recording capability (such as a camcorder). While stereo or multi-view imaging devices are very useful in the present disclosure, it is not necessary to employ such geometries or configurations, and the present disclosure is not so limited. Likewise, although it is preferred that the image acquisition device be a digital device, it is not necessary. For example, the image acquisition device could be an analog TV camera that acquires an initial image which is then processed into a digital image (for example, via an analog-to-digital device like a commercial-off-the-shelf frame grabber) for further use in the method of the present disclosure. The image acquisition device may be coupled to a processor 1725 (e.g. a processing system), shown incorporated in the image processor 1730 in FIG. 17, to control the imaging operation and process image data.

Typically, the processor 1725 operates as a data processing device, for example, it may be incorporated into a computer. The processor 1725 may include a central processing unit or parallel processor, and input/output interface, a memory with a program, wherein all the components may be connected by a bus. Further, the computer may include an input device, a display, and may also include one or more secondary storage devices. The bus may be internal to the computer and may include an adapter for receiving a keyboard or input device or may include external connections.

The processor 1725 may execute a program that may be configured to include predetermined operations. The processor may access the memory in which may be stored at least one sequence of code instructions comprising the program for performing predetermined operations. The memory and the program may be located within the computer or may be located external thereto. By way of example, and not limitation, a suitable image processor 1730 may be a digital processing system which includes one or more processors or other type of device. For example, a processor and/or an image processor may be a controller or any type of personal computer ("PC"). Alternatively, the processor may comprise an Application Specific Integrated Circuit (ASIC) or Field Programmable Gate Array (FPGA). It will be understood by those of ordinary skill in the art that the processor and/or the image processor for use with the present disclosure is programmed and configured to perform various known image processing techniques, for example, segmentation, edge detection, object recognition and selection. These techniques are generally known and do not need to be separately described here. The methods described herein may be implemented on various general or specific purpose computing systems. In certain embodiments, the methods of the present application may be implemented on a specifically configured personal computer or workstation. In other embodiments, the methods may be implemented on a general-purpose workstation, including one connected to a network. Alternatively or additionally, the methods of the disclosure may be, at least partially, implemented on a card for a network device or a general-purpose computing device. The processor/image processor may also include memory, storage devices, and other components generally known in the art and, therefore, they do not need to be described in detail here. The image processor could be used in conjunction with various manual, partially automated and fully automated (including robotic) systems and devices.

The imaging display device 1740 may comprise a high resolution computer monitor which may optionally be a touch screen. Alternatively, the imaging display device 1740 can be other touch sensitive devices, including tablet, pocket PC, and other plasma screens.

Methods and apparatuses (e.g., devices, systems, etc.) of the present disclosure may be carried out by providing a modification interface, or user modification interface, including touch screen, clickable icons, selection buttons in a menu, dialog box, or a roll-down window of an interface that may be provided to feed into the computer. According to another embodiment, the imaging display device 1740 may display the selection window and a stylus or keyboard for entering a selection, for example, directly on the display itself. According to one embodiment, commands may be input via the modification interface through a programmable stylus, keyboard, mouse, speech processing system, laser pointer, touch screen, tablet computer, personal digital assistant (PDA), a remote input device (such as a pendant), or other input mechanism. The remote input device may include clickable icons, selection buttons, dialog boxes, or roll-down windows which are the same as or similar to those found on the user modification interface. In yet another embodiment, the remote input device may be configured to accommodate additional modification controls. Moreover, either the remote input device or any other input mechanism may have icons which allow the user to control the robotic arm, allowing the user move the robotic arm away from the patient, or incorporate a STOP button, enabling the user to terminate operation of the robotic arm or the tool (e.g., device for delivery of electrical therapy) in the event of an emergency. Alternatively, the modification interface may comprise a dedicated piece of hardware. In some embodiments the selections or adjustment made through the modification interface may be executed by code instructions that may be executed on the computer processor.

Embodiments of the methods of the present disclosure may be implemented using computer software, firmware or hardware. Various programming languages and operating systems may be used to implement the present disclosure. The program that runs the method and system may include a separate program code including a set of instructions for performing a desired operation or may include a plurality of modules that perform such sub-operations of an operation or may be part of a single module of a larger program providing the operation. The modular construction facilitates adding, deleting, updating and/or amending the modules therein and/or features within the modules.

In some embodiments, a user may select a particular method or embodiment of this application, and the processor will run a program or algorithm associated with the selected method. In certain embodiments, various types of position sensors may be used. For example, in certain embodiment, a non-optical encoder may be used where a voltage level or polarity may be adjusted as a function of encoder signal feedback to achieve a desired angle, speed, or force.

The processor for use in the present disclosure may comprise any suitable device programmed and configured to perform various methods described in detail in the present application. In some embodiments modification may be accomplished through the modification interface. For example, the processor for use in the present disclosure may be a processor comprising a set of instructions for executing operations, the set of instructions including instructions capable of being executed by a processor of an electrical therapy apparatus, that, when executed by the processor, causes the electrical therapy apparatus to apply electrical energy and also move the one or more electrodes to prevent arcing. As mentioned above, in any of the robotic systems descried herein the driver may be the robotic arm. The system for use according to the disclosures described herein may comprise in some implementations in addition to a processor an image acquisition device.

In some embodiments, the system may comprise a user input device, the user input device configured to allow a user to interactively modify the movement (including triggering, frequency, etc.) of the one or more electrodes and/or the applied energy. In other embodiments, the processor is configured to automatically modify the movement of the one or more electrodes during a treatment procedure (e.g., when applying an energy therapy).

Certain embodiments relate to a machine-readable medium (e.g., computer readable media) or computer program products that include program instructions and/or data (including data structures) for performing various computer-implemented operations. A machine-readable medium may be used to store software and data which causes the system to perform methods of the present disclosure. The above-mentioned machine-readable medium may include any suitable medium capable of storing and transmitting information in a form accessible by processing device, for example, a computer. Some examples of the machine-readable medium include, but not limited to, magnetic disc storage such as hard disks, floppy disks, magnetic tapes. I may also include a flash memory device, optical storage, random access memory, etc. The data and program instructions may also be embodied on a carrier wave or other transport medium. Examples of program instructions include both machine code, such as produced by a compiler, and files containing higher level code that may be executed using an interpreter.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc.

Any numerical values given herein should also be understood to include about or approximately that value unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the disclosure. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

Various embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A system for delivery of electrical therapy, the system comprising:
   one or more penetrating electrodes configured to deliver electrical energy to a tissue;
   a driver coupled to and configured to move the one or more penetrating electrodes to rotate, oscillate, or both rotate and oscillate the one or more penetrating electrodes; and
   one or more processors configured to: 1) cause application of a high voltage power, having a peak voltage of between 0.5 kilovolts per centimeter (kV/cm) and 500 kV/cm, to the one or more penetrating electrodes and 2) direct operation of the driver to move the one or more penetrating electrodes when the high voltage power is applied to the one or more penetrating electrodes or between pulses of pulsed applied power to the one or more penetrating electrodes,
   wherein the one or more processors are further configured to prevent or reduce arcing while applying the electrical energy to the tissue by controlling movement of the one or more penetrating electrodes to move a point of high current density to a different location in the tissue.

2. The system of claim 1, wherein the one or more penetrating electrodes comprises one or more of: a needle electrode, a blade electrode.

3. The system of claim 1, wherein the driver is configured to oscillate by translationally reciprocating the one or more penetrating electrodes.

4. The system of claim 1, further comprising a linkage coupling the driver to the one or more penetrating electrodes, wherein the linkage is configured to translate the movement of the driver into rotation, translational oscillation or both rotation and translation oscillation of the one or more penetrating electrodes.

5. The system of claim 4, wherein the linkage comprises a flexible shaft.

6. The system of claim 4, wherein the linkage comprises one or more gears or a lead screw.

7. The system of claim 4, wherein the linkage is configured to translate movement of the driver into rotation of the one or more penetrating electrodes about a central axis through each or at least some of the one or more penetrating electrodes.

8. The system of claim 4, wherein the linkage is configured to translate the movement of the driver into oscillatory movement in a long axis of or at least some of the one or more penetrating electrodes.

9. The system of claim 4, wherein the linkage is configured to translate the movement of the driver into oscillatory side-to-side movement of each or at least some of the one or more penetrating electrodes.

10. The system of claim 4, wherein the linkage is configured to translate the movement of the driver into oscillatory pitch, yaw or tilt movement of each or at least some of the one or more penetrating electrodes.

11. The system of claim 1, wherein the driver comprises a solenoid configured to drive oscillation of the one or more penetrating electrodes.

12. The system of claim 11, further comprising a linkage between the driver and the one or more penetrating electrodes, wherein the linkage is configured to translate oscillation of the solenoid into rotation and/or translational oscillation of the one or more penetrating electrodes.

13. The system of claim 1, wherein the driver comprises electromagnetic coils configured to move a magnet.

14. The system of claim 13, further comprising a linkage between the one or more penetrating electrodes and the driver, wherein the linkage is configured to translate the movement of the magnet into rotation and/or translational oscillation of the one or more penetrating electrodes.

15. The system of claim 1, wherein a single processor of the one or more processors causes the application of the high voltage power and directs operation of the driver.

16. The system of claim 1, wherein the driver is configured to rotate, oscillate or rotate and oscillate the one or more penetrating electrodes at between 0.01 Hz and 10 kHz.

17. The system of claim 1, the system further comprising at least one robotic arm, wherein the one or more penetrating electrodes is coupled to the at least one robotic.

18. The system of claim 17, wherein a first processor of the one or more processors is configured to cause application of the high voltage power and a second processor of the one or more processors is configured to direct operation of the driver.

19. The system of claim 17, wherein the driver comprises a motor configured to rotate, oscillate or rotate and oscillate.

20. The system of claim 17, wherein the one or more processors control operation of the at least one robotic arm.

21. The system of claim 17, further comprising a controller configured to coordinate application of the high voltage power during or between movement of the one or more penetrating electrodes.

22. The system of claim 17, further comprising an image acquisition device, wherein the at least one robotic arm is configured to be moved based at least in part on an image or data acquired by the image acquisition device.

23. The system of claim 1, wherein the electrical energy comprises sub-microsecond pulsed electric fields.

24. The system of claim 23, wherein the electrical energy comprises nanosecond pulses having a peak voltage greater than 5 kV/cm.

25. The system of claim 1, further comprising a main shaft, the main shaft includes or is operatively connected to one or more sub-shafts, wherein the one or more sub-shafts and the one or more penetrating electrodes are held by a frame and each of the one or more penetrating electrodes is configured to rotate within its individual long axis within the frame.

* * * * *